(12) United States Patent
Lavon et al.

(10) Patent No.: US 8,974,430 B2
(45) Date of Patent: Mar. 10, 2015

(54) ABSORBENT ARTICLE COMPRISING AN ACTIVATED REGION

(75) Inventors: Gary Dean Lavon, Liberty Township, OH (US); Thomas Henrich, Montgomery, OH (US); Luke Nogales, West Chester, OH (US); Kevin Michael Smith, Cincinnati, OH (US); John Strube, Okeana, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 803 days.

(21) Appl. No.: 12/434,934

(22) Filed: May 4, 2009

(65) Prior Publication Data

US 2009/0312732 A1 Dec. 17, 2009

Related U.S. Application Data

(60) Provisional application No. 61/073,154, filed on Jun. 17, 2008, provisional application No. 61/174,688, filed on May 1, 2009, provisional application No. 61/174,694, filed on May 1, 2009.

(51) Int. Cl.
*A61F 13/15* (2006.01)
*A61F 13/494* (2006.01)
*A61F 13/49* (2006.01)

(52) U.S. Cl.
CPC ..... *A61F 13/49453* (2013.01); *A61F 13/49413* (2013.01); *A61F 13/49012* (2013.01)
USPC ............. 604/385.04; 604/385.22; 604/385.27

(58) Field of Classification Search
USPC ............................ 604/385.04, 385.24–385.28
See application file for complete search history.

(56) References Cited

U.S. PATENT DOCUMENTS

| | | | |
|---|---|---|---|
| 3,848,594 A | 11/1974 | Buell |
| 4,662,875 A | 5/1987 | Hirotsu et al. |
| 4,775,375 A | 10/1988 | Aledo |
| 4,846,815 A | 7/1989 | Scripps |
| 4,894,060 A | 1/1990 | Nestegard |
| 4,940,464 A | 7/1990 | Van Gompel |

(Continued)

OTHER PUBLICATIONS

International Search and Written Opinion, PCT/US2009/047658, date of mailing Sep. 21, 2009.

(Continued)

*Primary Examiner* — Melanie Hand
(74) *Attorney, Agent, or Firm* — Richard L. Alexander

(57) ABSTRACT

An absorbent article may comprise an absorbent assembly comprising an absorbent core. The article may also comprise a chassis formed by a web comprising at least one continuous layer that forms a portion of a water-impermeable backsheet and a portion of laterally opposing side flaps. The chassis may further comprise a longitudinal axis, a lateral axis, a front waist region comprising a front waist edge, a back waist region comprising a back waist edge, a crotch region between the waist regions, laterally opposing side edges extending between the front waist edge and the back waist edge, an exterior surface, and an interior surface to which the absorbent assembly is attached. The attachment of the absorbent assembly may be shaped. The chassis may further comprise a continuously activated region disposed in one or both of the front and back waist regions of the article. The continuously activated region may comprise longitudinally oriented ridges and valleys, wherein the continuously activated region overlaps the portion of the chassis where at least one abdominal stretch panel is disposed.

20 Claims, 14 Drawing Sheets

(56) References Cited

U.S. PATENT DOCUMENTS

| | | |
|---|---|---|
| 4,946,527 A | 8/1990 | Battrell |
| 4,950,264 A | 8/1990 | Osborn |
| 5,092,861 A | 3/1992 | Nomura |
| 5,151,092 A | 9/1992 | Buell |
| 5,221,274 A | 6/1993 | Buell |
| 5,246,433 A | 9/1993 | Hasse |
| 5,366,782 A | 11/1994 | Curro |
| 5,518,801 A | 5/1996 | Chappell |
| 5,569,234 A | 10/1996 | Buell |
| 5,897,545 A | 4/1999 | Kline |
| 5,957,908 A | 9/1999 | Kline |
| 5,997,521 A | 12/1999 | Robles et al. |
| 6,120,487 A | 9/2000 | Ashton |
| 6,120,489 A | 9/2000 | Johnson |
| 6,251,097 B1 | 6/2001 | Kline |
| 6,432,098 B1 | 8/2002 | Kline |
| 6,648,869 B1 | 11/2003 | Gillies et al. |
| 6,669,618 B2 | 12/2003 | Reising |
| 6,790,202 B2 | 9/2004 | Klemp et al. |
| 6,962,578 B1 | 11/2005 | LaVon |
| 7,341,579 B2 | 3/2008 | Kinoshita |
| 7,695,463 B2 | 4/2010 | LaVon et al. |
| 7,737,324 B2 | 6/2010 | LaVon et al. |
| 7,799,006 B2 | 9/2010 | Kline |
| 7,972,316 B2 | 7/2011 | Toyoshima et al. |
| 8,075,543 B2 | 12/2011 | Okuda |
| 2003/0088220 A1 | 5/2003 | Molander |
| 2003/0233082 A1 | 12/2003 | Kline |
| 2005/0130821 A1 | 6/2005 | Reising |
| 2005/0215970 A1 | 9/2005 | Kline |
| 2005/0215971 A1* | 9/2005 | Roe et al. ............... 604/385.27 |
| 2005/0234419 A1 | 10/2005 | Kline |
| 2007/0074381 A1 | 4/2007 | Raycheck |
| 2007/0078426 A1 | 4/2007 | Kline |
| 2007/0078427 A1 | 4/2007 | Raycheck |
| 2008/0107861 A1 | 5/2008 | Dalal |
| 2008/0208156 A1 | 8/2008 | LaVon |
| 2008/0234649 A1 | 9/2008 | Hamall |
| 2009/0312730 A1 | 12/2009 | LaVon |
| 2009/0312735 A1 | 12/2009 | LaVon |
| 2009/0312737 A1 | 12/2009 | LaVon |
| 2009/0312738 A1 | 12/2009 | LaVon |
| 2010/0280478 A1 | 11/2010 | LaVon et al. |
| 2010/0292663 A1 | 11/2010 | LaVon et al. |

OTHER PUBLICATIONS

All Office Actions, U.S. Appl. No. 12/779,434.
All Office Actions, U.S. Appl. No. 12/770,862.

* cited by examiner

ABSORBENT ARTICLE COMPRISING AN ACTIVATED REGION

This application claims the benefit of U.S. Provisional Application Nos. 61/073,154 filed Jun. 17, 2008, and 61/174,688 and 61/174,694, both filed on May 1, 2009, the substances of which are incorporated herein by reference.

FIELD OF THE INVENTION

Background of the Invention

Disposable absorbent articles are designed to absorb and contain bodily waste in order to prevent soiling of the body and clothing of the wearer, as well as bedding or other objects with which the wearer comes into contact. As the usage of disposable absorbent articles has expanded, their complexity has increased with the incorporation of additional features serving to enhance their performance and appearance. The costs of the materials and the costs of the manufacturing processes have also increased in conjunction with the increase in complexity. As a result, the prices at which these articles are sold have risen to levels that many potential purchasers around the world cannot afford to pay. Thus, a need exists for a simple disposable absorbent article. One approach to delivering a simple, affordable absorbent article is described herein. The approach described herein leverages simplicity of design and material efficiency enabled via activation to deliver a simplistic low cost article. The activation of the chassis web renders portions of a simple plastic film extensible and somewhat elastic. This extensibility allows for increased flexibility with regard to fit and sizing, as well as delivering significant wearer comfort. Delivering a high degree of extensibility of a complete absorbent article that comprises a non-extensible absorbent assembly requires holistic integration of the absorbent assembly into the extensible chassis. This integration is achieved via differential (zoned) activation and attachment of the absorbent assembly in a complimentary fashion thereby minimizing the impact of the non-extensible absorbent assembly on the extensibility of the absorbent article provided by the zoned activation. The combination of the highly extensible chassis, complimentarily attached absorbent assembly and abdominal stretch panels provide a structure that has the look and feel of real underwear when compared to other less extensible highly contracted diapers. This underwear look and feel is important to both the caregiver and the wearer, especially in a toilet training context, since it conveys a transition from being a "baby" to becoming a "big boy or big girl."

SUMMARY OF THE INVENTION

An absorbent article may comprise an absorbent assembly comprising an absorbent core. The article may also comprise a chassis formed by a web comprising at least one continuous layer that forms a portion of a water-impermeable backsheet and a portion of laterally opposing side flaps. The chassis may further comprise a longitudinal axis, a lateral axis, a front waist region comprising a front waist edge, a back waist region comprising a back waist edge, a crotch region between the waist regions, laterally opposing side edges extending between the front waist edge and the back waist edge, an exterior surface, and an interior surface to which the absorbent assembly is attached. Each of the side flaps may comprise a longitudinally extending first elastic gathering member attached at or adjacent to its proximal edge.

The article may also comprise at least one abdominal stretch panel attached to the interior surface or the exterior surface of the chassis in the front waist region or the back waist region. The abdominal stretch panel may have a circumferentially extending longitudinally distal edge disposed at or adjacent to the respective waist edge and a longitudinally opposing circumferentially extending longitudinally proximal edge. The abdominal stretch panel may provide a circumferential contractive force around the waist opening when the chassis is stretched circumferentially.

The chassis may further comprises a continuously activated region disposed in one or both of the front and back waist regions of the article. The continuously activated region may comprise longitudinally oriented ridges and valleys, wherein the continuously activated region overlaps the portion of the chassis where the at least one abdominal stretch panel is disposed.

BRIEF DESCRIPTION OF THE DRAWINGS

In the accompanying drawing figures, like reference numerals identify like elements, which may or may not be identical in the several exemplary embodiments that are depicted. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description.

In the drawing figures and in the written description, lowercase letters appended to reference numerals indicate generally symmetric elements, e.g., left and right symmetric elements may be respectively identified by the reference numerals 1$a$ and 1$b$. A reference numeral without an appended lowercase letter identifies all of the elements to which that particular reference numeral applies, e.g., the same elements as a group may be designated 1.

The edges of various components are shown offset from each other for clarity; the depiction of parallel edges immediately adjacent to each other is intended to represent that these edges are disposed either collinearly or in close proximity to each other.

Figure 1:
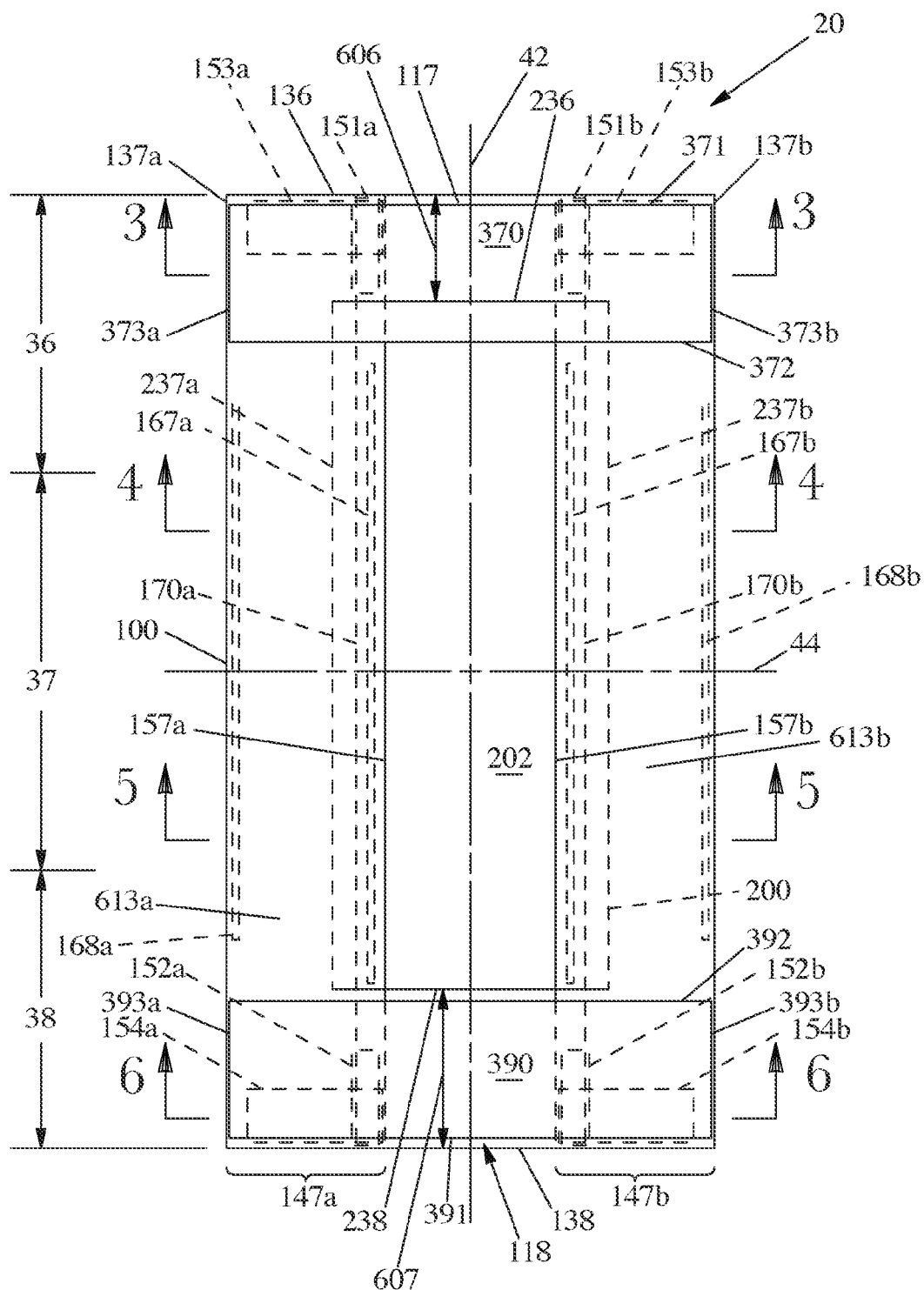

FIG. 1 is a plan view of an exemplary disposable absorbent article in the form of a diaper 20, which is shown in its flat, uncontracted state, i.e., without the contraction induced by elastic members. In FIG. 1, the interior of the diaper is shown facing the viewer.

Figure 2:
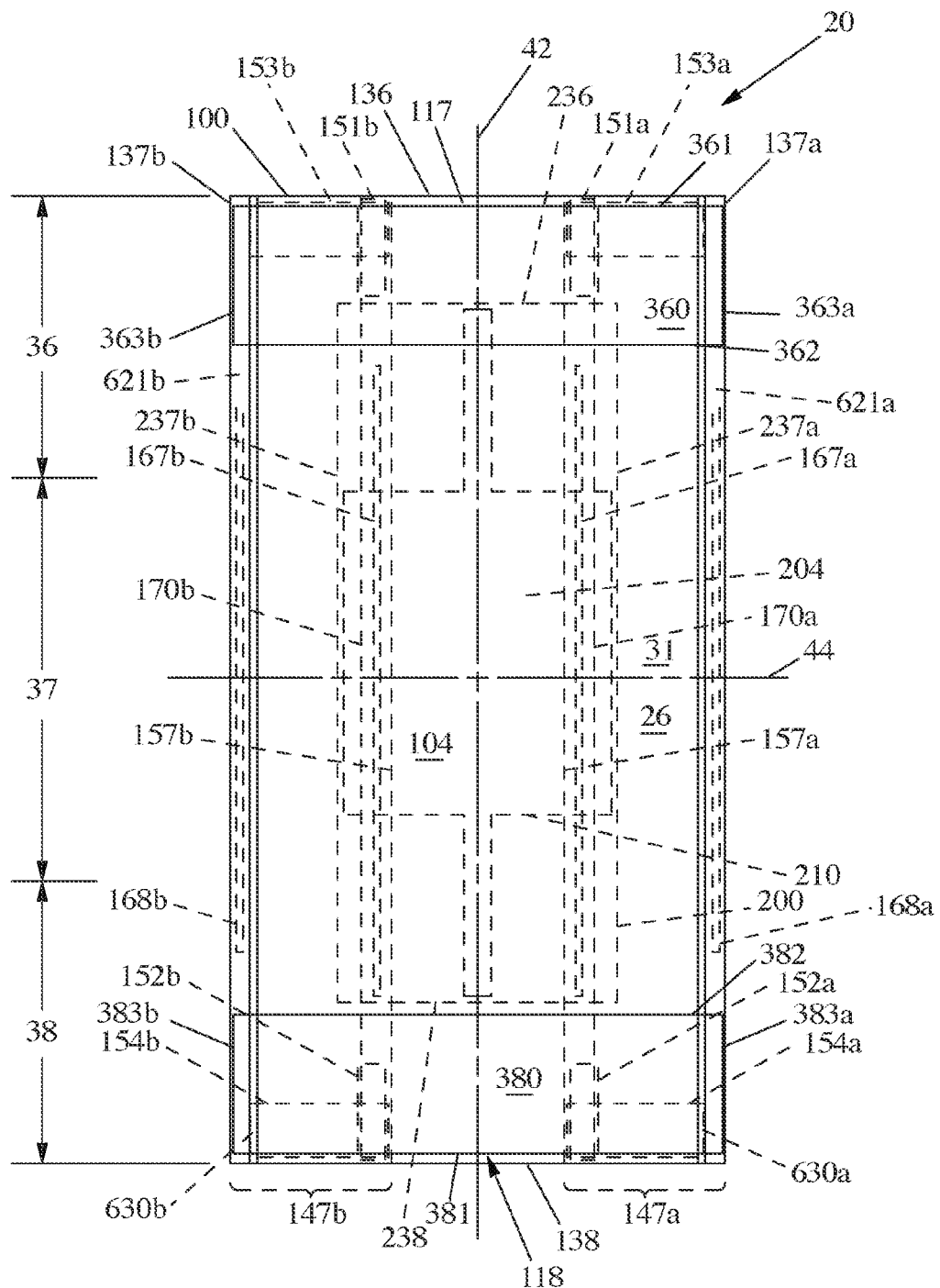

FIG. 2 is a plan view of the diaper 20 of FIG. 1 with the exterior portion of the diaper 20 shown facing the viewer.

Figure 3:
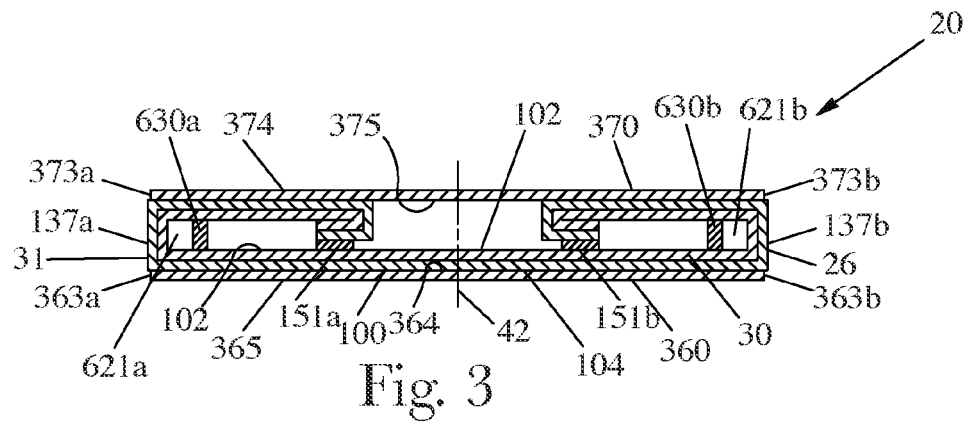

FIG. 3 is a section view of the diaper 20 of FIG. 1 taken at the section line 3-3.

Figure 4:
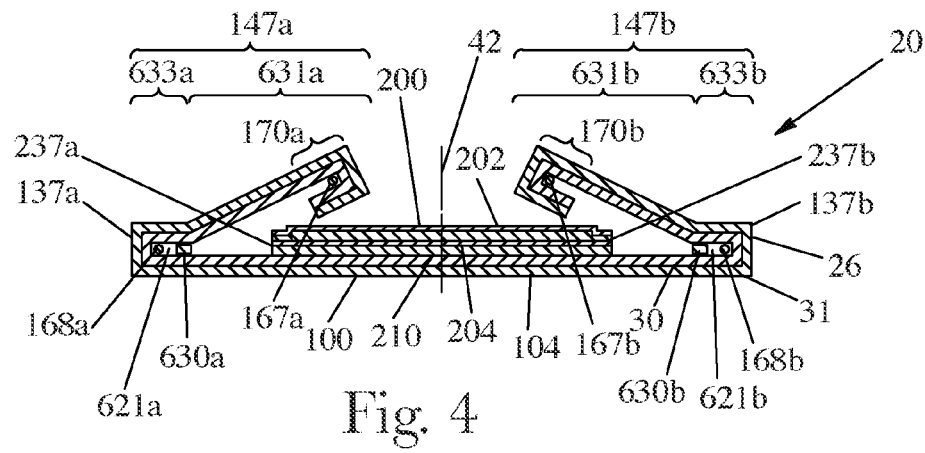

FIG. 4 is a section view of the diaper 20 of FIG. 1 taken at the section line 4-4.

Figure 5:
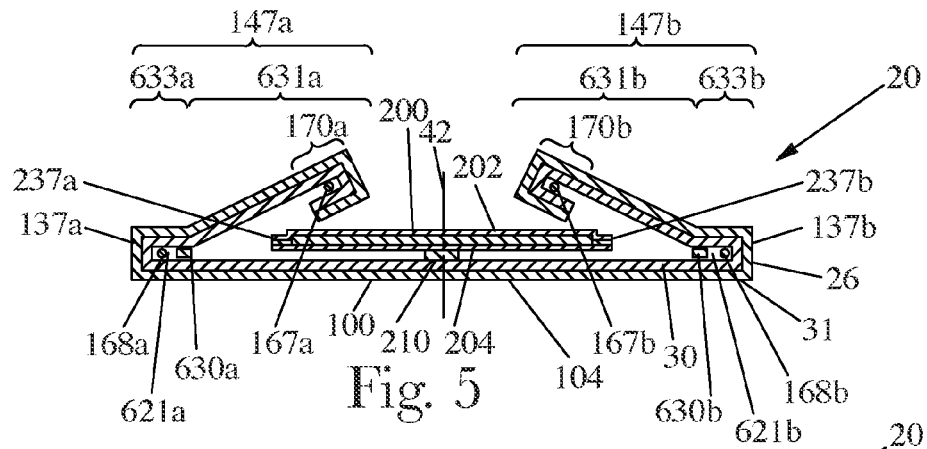

FIG. 5 is a section view of the diaper 20 of FIG. 1 taken at the section line 5-5.

Figure 6:
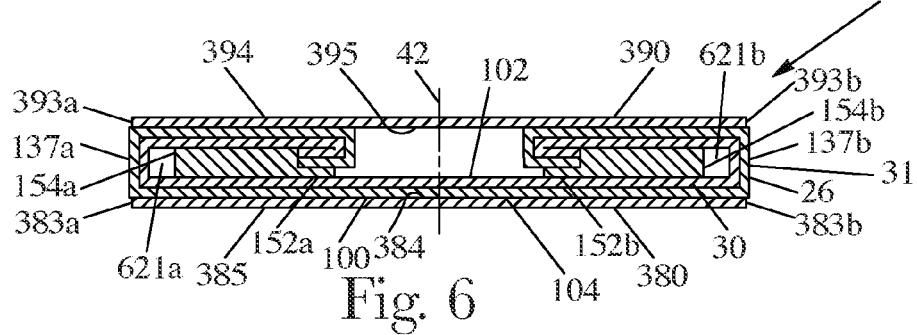

FIG. 6 is a section view of the diaper 20 of FIG. 1 taken at the section line 6-6.

Figure 7:
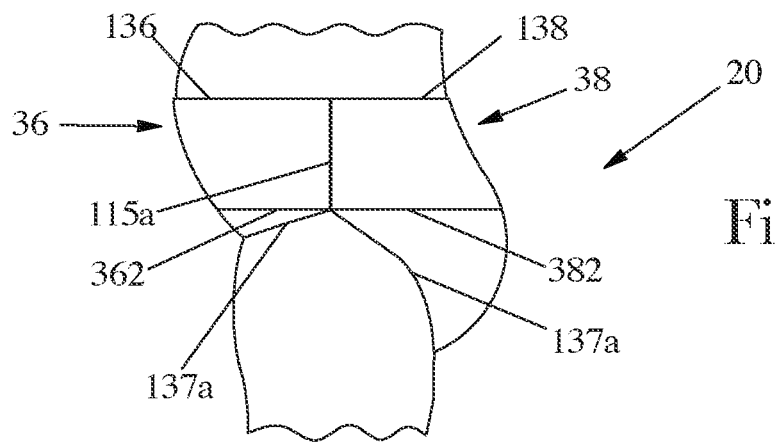

FIG. 7 is a simplified side elevation view of an exemplary diaper 20 of FIG. 1 being worn about a lower torso of a wearer.

Figure 8:
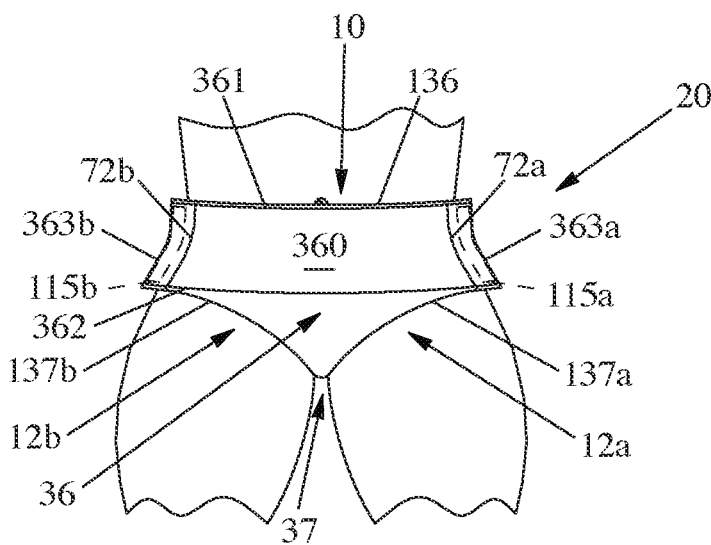

FIG. 8 is a front elevation view of the diaper 20 of FIG. 7.

Figure 9:
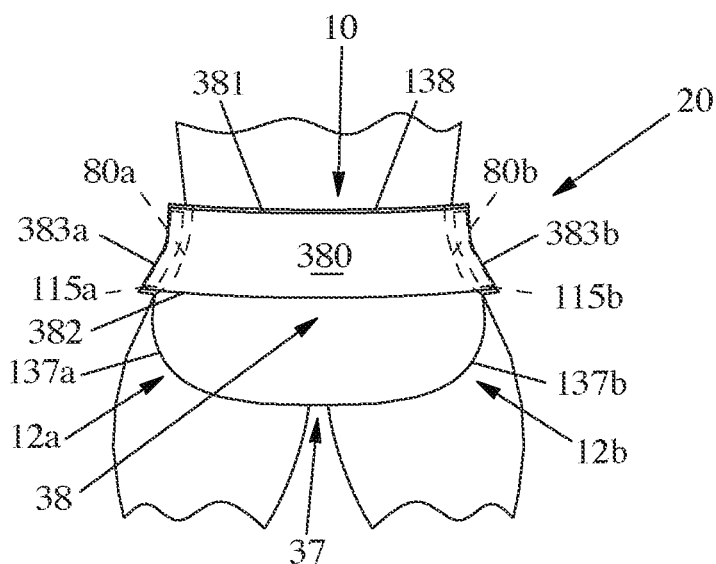

FIG. 9 is a back elevation view of the diaper 20 of FIG. 7.

Figure 10:
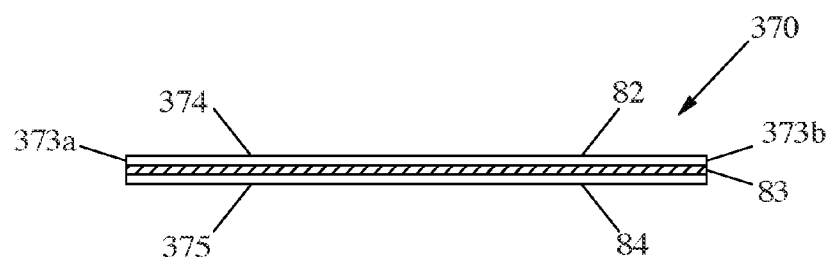

FIG. 10 is an elevation view of a laminate stretch panel.

Figure 11:
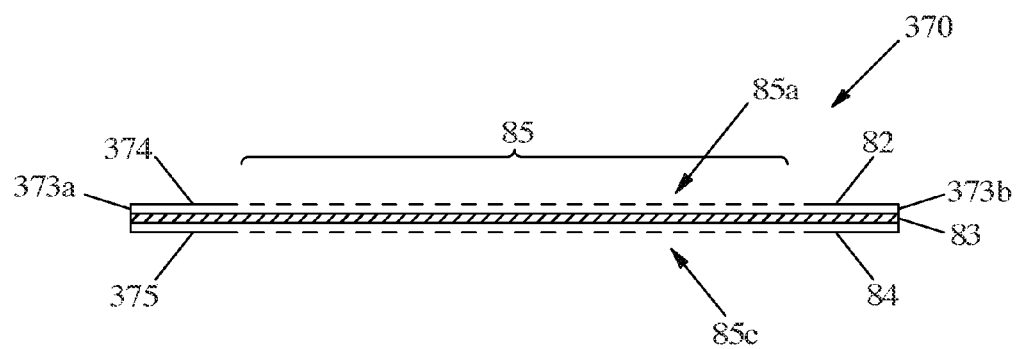

FIG. 11 is a view of the laminate stretch panel of FIG. 10 in a stretched condition.

Figure 12:
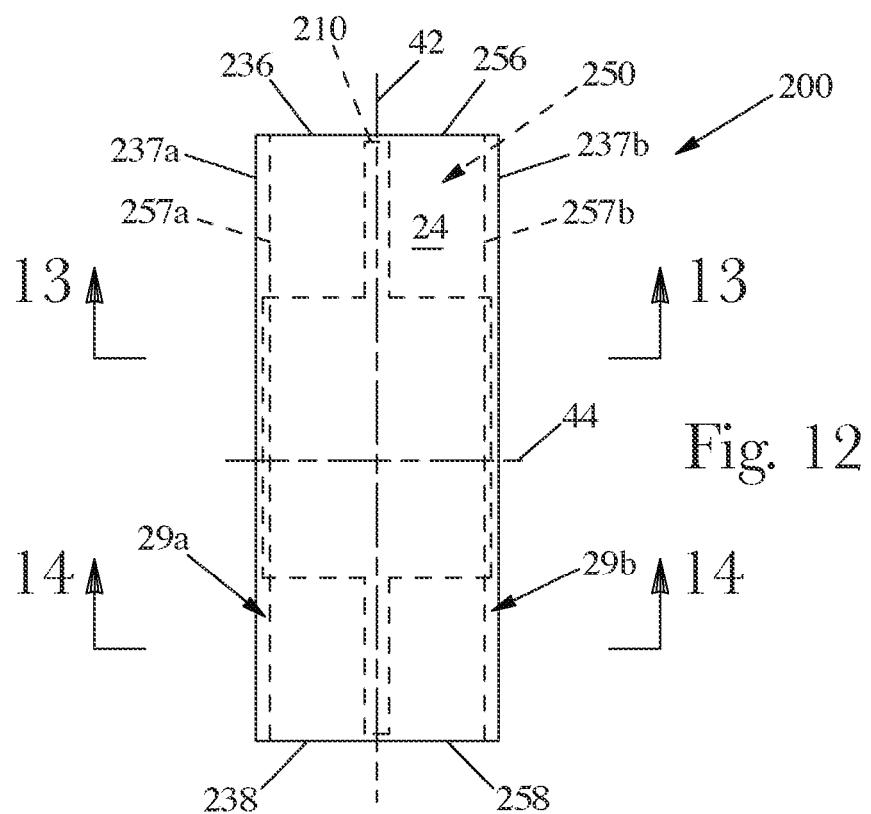

FIG. 12 is a plan view of an exemplary absorbent assembly 200 with the interior portion of the absorbent assembly 200 shown facing the viewer.

Figure 13:
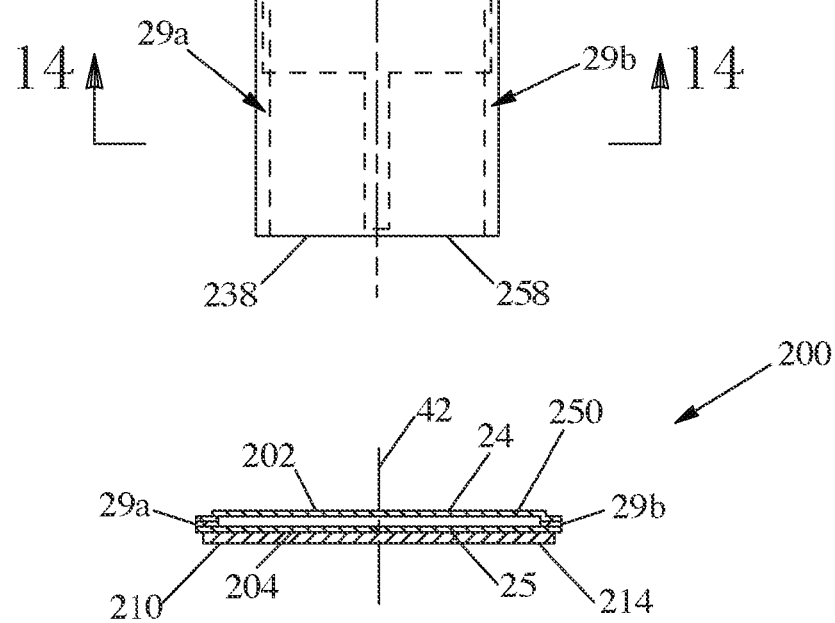

FIG. 13 is a section view of the absorbent assembly of FIG. 12 taken at the section line 13-13.

Figure 14:
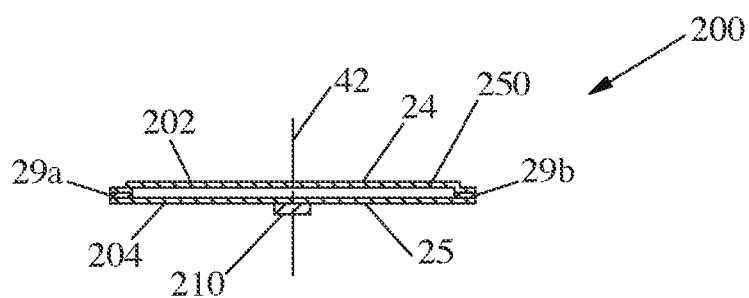

FIG. 14 is a section view of the absorbent assembly of FIG. 12 taken at the section line 14-14.

Figure 15:
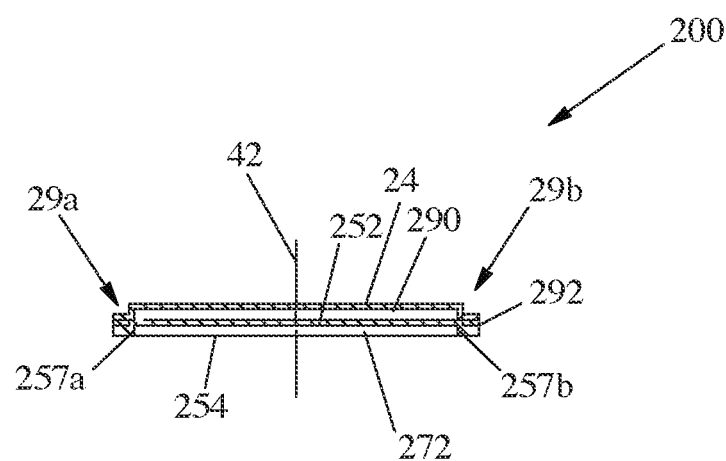

FIG. 15 is a section view of an alternative embodiment of the absorbent assembly 200 of FIG. 12.

Figure 16:
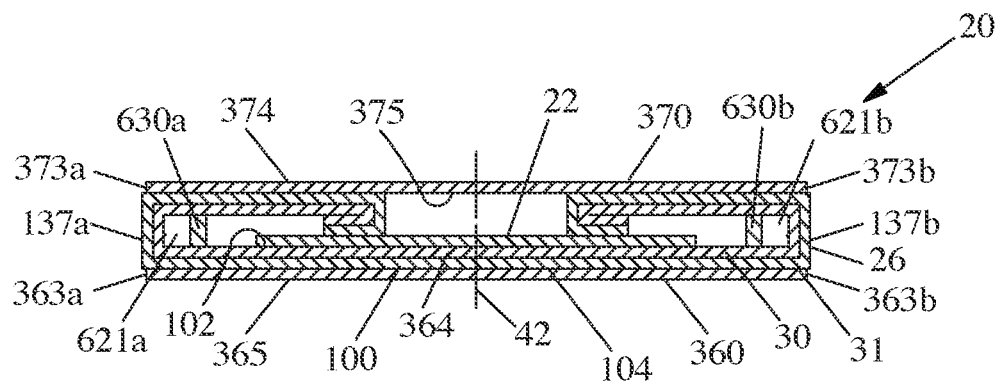

FIG. 16 is a section view of an alternative embodiment of diaper 20 of FIG. 1 comprising an inner liner taken at the section line 3-3.

Figure 17:
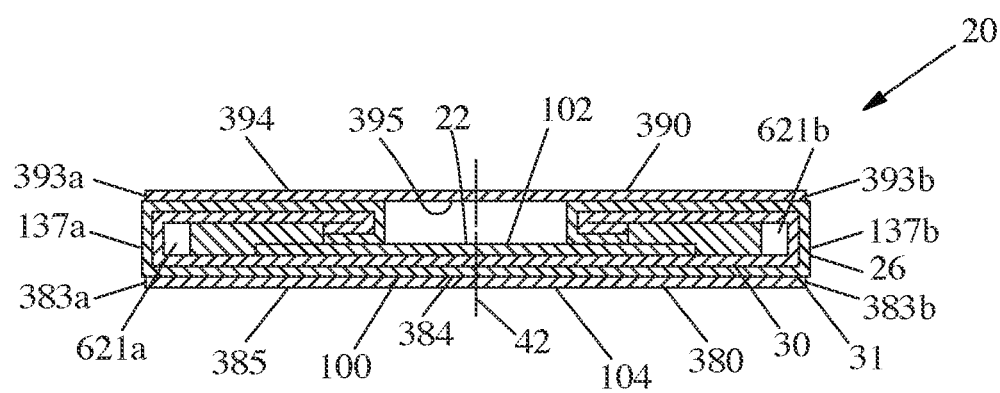

FIG. 17 is a section view of an alternative embodiment of diaper 20 of FIG. 1 comprising an inner liner taken at the section line 6-6.

Figure 18:
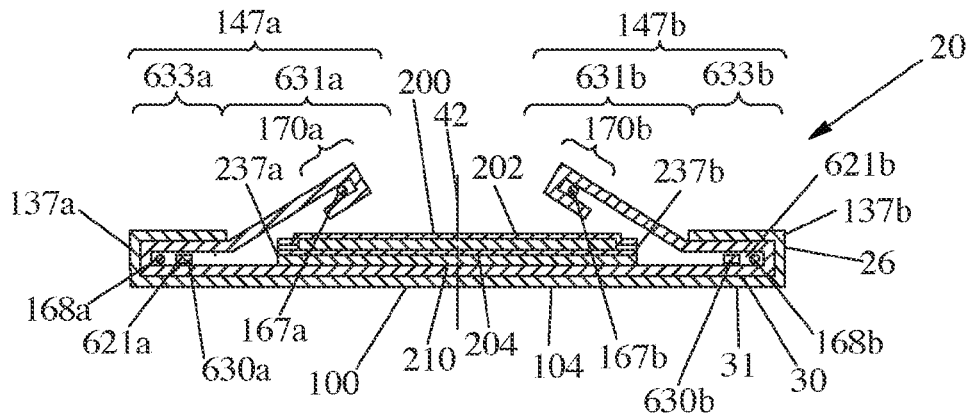

FIG. 18 is a section view of an alternative embodiment of the side flaps 147 of FIG. 1 taken at the section line 4-4.

Figure 19:
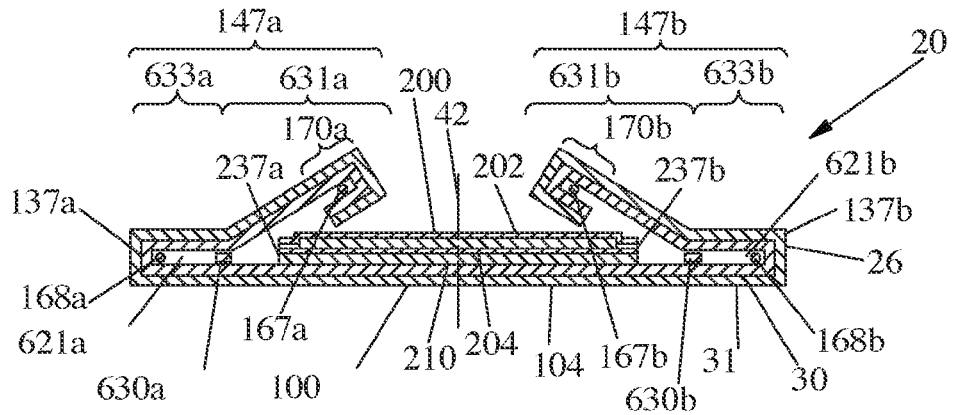

FIG. 19 is a section view of an alternative embodiment of the side flaps 147 of FIG. 1 taken at the section line 4-4.

Figure 20:
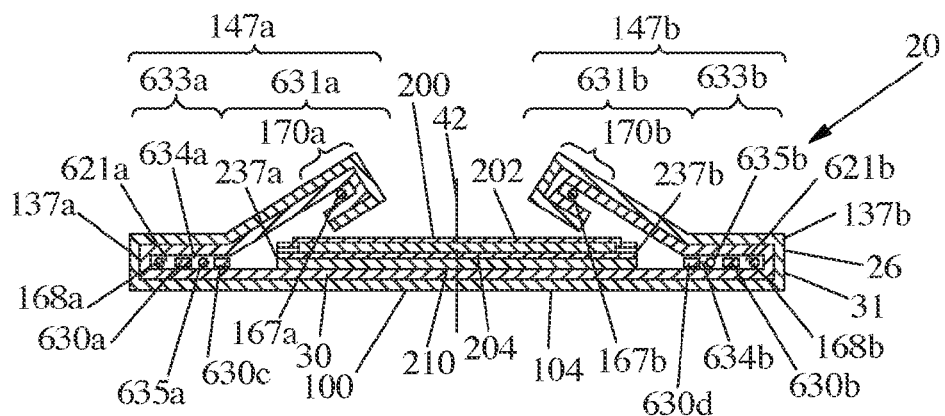

FIG. 20 is a section view of an alternative embodiment of the side flaps 147 of FIG. 1 taken at the section line 4-4.

Figure 21:
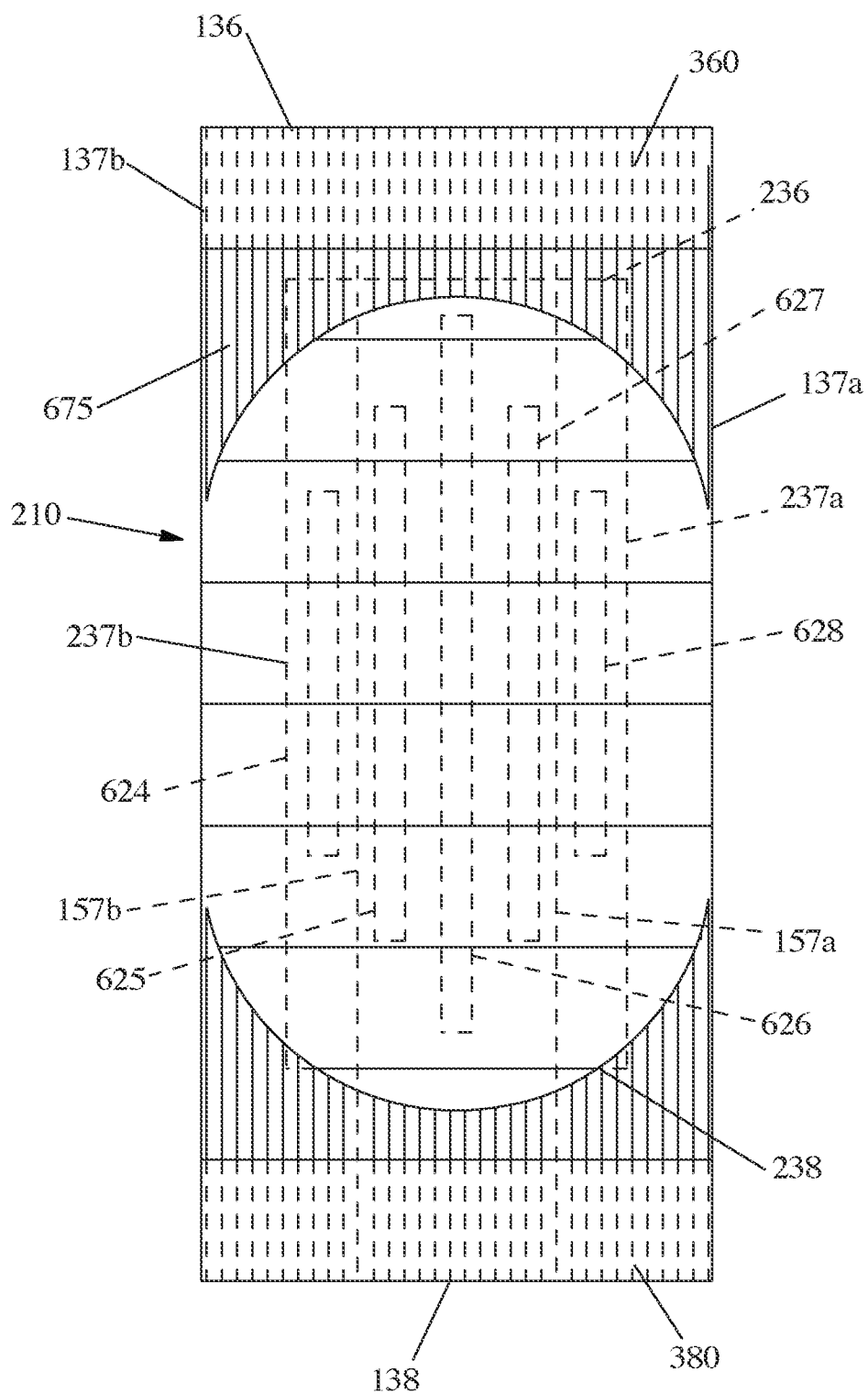

FIG. 21 is a plan view of an alternative embodiment of an activation and attachment pattern 675 and 210 of FIG. 1, which is shown in its flat, uncontracted state, i.e., without the contraction induced by elastic members. In FIG. 21, the exterior of the diaper is shown facing the viewer.

Figure 22:
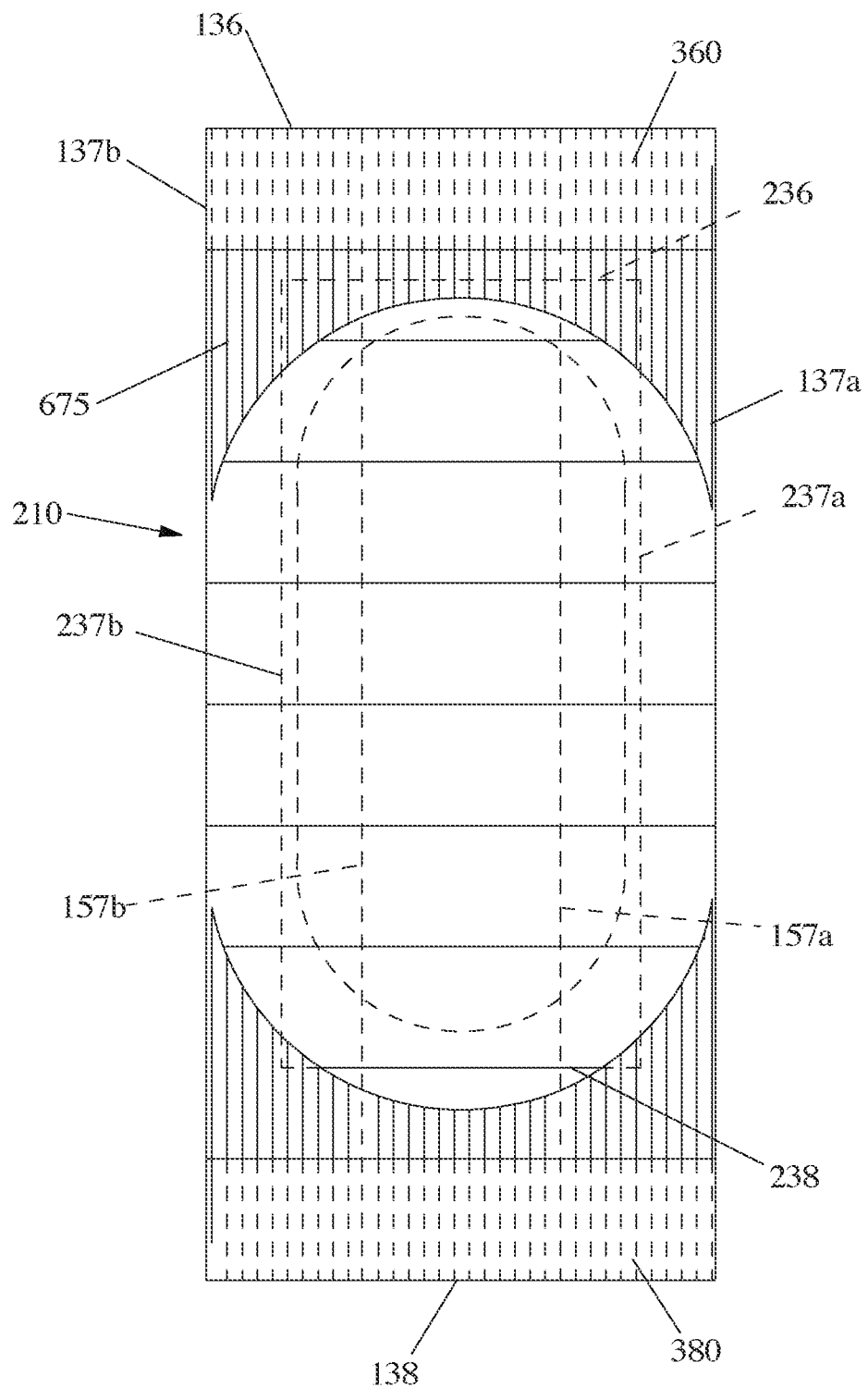

FIG. 22 is a plan view of an alternative embodiment of an attachment pattern 210 of FIG. 1, which is shown in its flat, uncontracted state, i.e., without the contraction induced by elastic members. In FIG. 22, the exterior of the diaper is shown facing the viewer.

Figure 23:
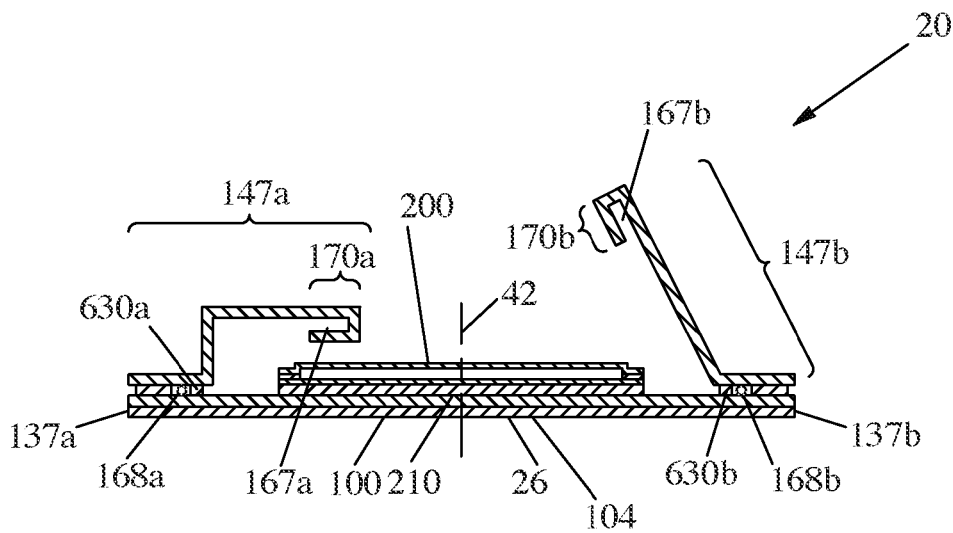

FIG. 23 is a section view of an alternative embodiment of the side flaps 147 of FIG. 1 comprising attached side flaps taken at the section line 4-4.

Figure 24:
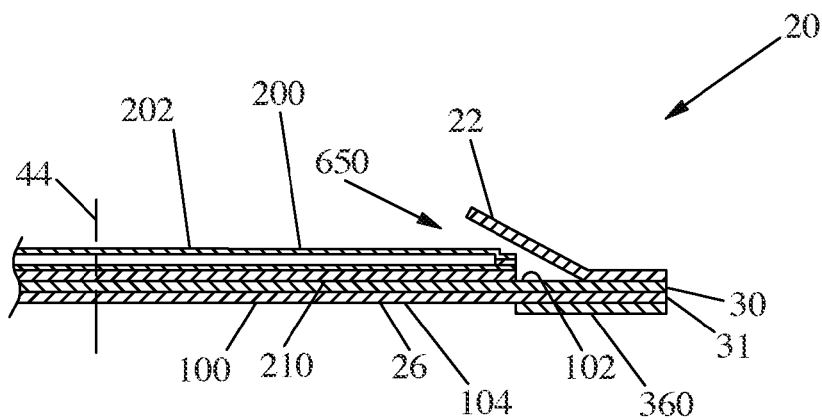

FIG. 24 is a section view of the abdominal stretch panel 370 of FIG. 1 taken along the longitudinal axis 42.

Figure 25:
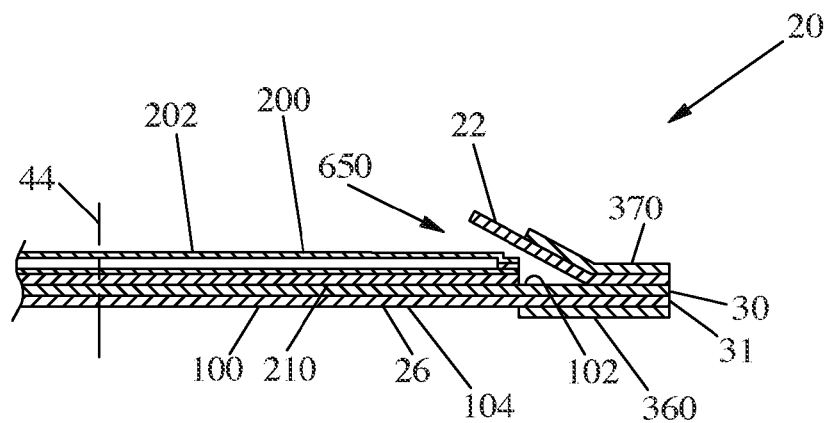

FIG. 25 is a section view of an alternative embodiment of the diaper 20 of FIG. 1 taken along the longitudinal axis 42 comprising an inner liner.

Figure 26:
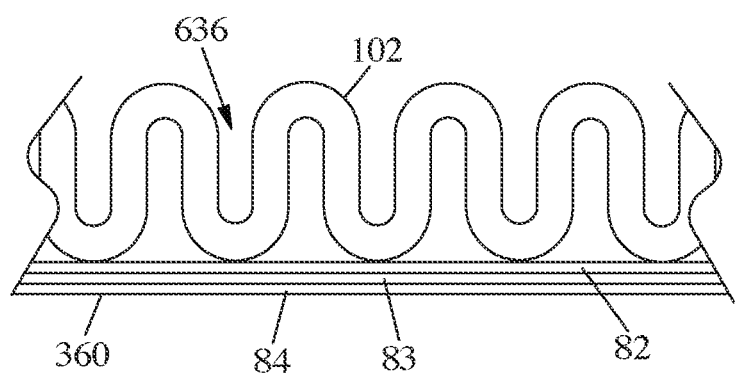

FIG. 26 is a simplified section view of an alternative embodiment of the interior surface 102 of FIG. 1 taken at the section line 3-3.

Figure 27:
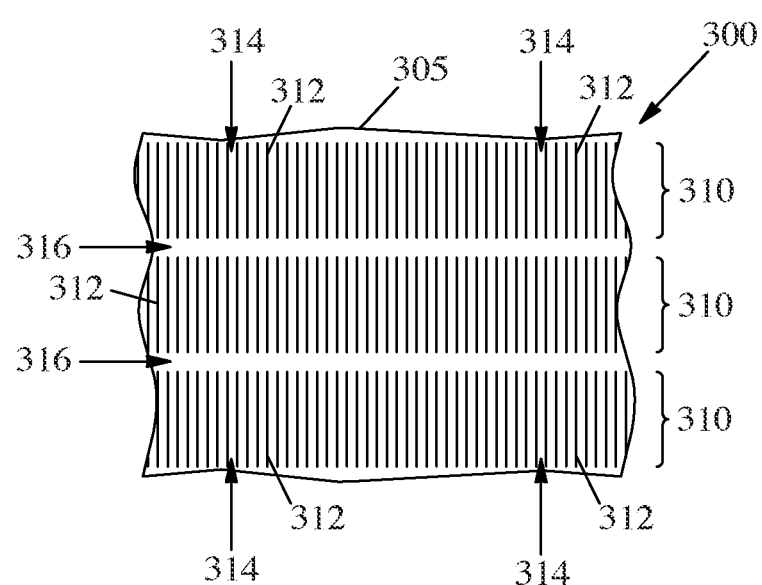

FIG. 27 is a plan view of an exemplary fragment of a formed web material.

DETAILED DESCRIPTION OF THE INVENTION

In this description, the following terms have the following meanings:

The term "absorbent article" refers to a device that absorbs and contains liquid, and more specifically, refers to a device that is placed against or in proximity to the body of the wearer to absorb and contain the various exudates discharged from the body.

The term "diaper" refers to an absorbent article that is generally worn by infants and incontinent persons about the lower torso and that is specifically adapted to receive and contain urinary and fecal waste. A diaper may be in the form of a taped diaper or a pull-on (pant style) diaper.

The term "disposable" refers to the nature of absorbent articles that generally are not intended to be laundered or otherwise restored or reused as an absorbent article, i.e., they are intended to be discarded after a single use and, may be recycled, composted or otherwise disposed of in an environmentally compatible manner.

The term "longitudinal" refers to a direction running from a waist edge to an opposing waist edge of the article and generally parallel to the maximum linear dimension of the article. Directions within 45° of the longitudinal direction are considered to be "longitudinal".

The term "lateral" refers to a direction running from a side edge to an opposing side edge of the article and generally at a right angle to the longitudinal direction. Directions within 45° of the lateral direction are considered to be "lateral".

The term "circumferential" refers to a direction encircling the waist of the wearer generally parallel to the lateral direction.

The term "disposed" refers to an element being attached and positioned in a particular place or position in a unitary structure with other elements.

The term "attach" refers to elements being connected or united by adhering, bonding, fastening etc., by any method suitable for the elements being attached together and their constituent materials. Many suitable means for attaching or joining elements together are well-known, including adhesive, pressure, thermal, mechanical, etc. Such attachment methods may be used to attach elements together over a particular area either continuously or intermittently. Unless indicated otherwise, elements that are described as being attached to each other are attached directly together, with either nothing or via one or more closure members, e.g., an adhesive or fastener, between them. Elements that are described as being attached to each other are attached together either permanently or temporarily, i.e., permanent attachment means that one or both of the elements and/or any closure members that are present must be functionally damaged in order to separate them such that they are not reattachable or refastenable and temporary attachment means that one or both of the elements and/or any closure members that are present may be separated and reattached or refastened (i.e., opened and closed) multiple times while substantially maintaining functionality of the closure member.

The term "laminate" refers to elements being attached together in a layered arrangement.

The terms "water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water to pass through its thickness in the absence of a forcing pressure. Conversely, the term "water-impermeable" refers to a layer or a layered structure through the thickness of which liquid water cannot pass in the absence of a forcing pressure. A layer or a layered structure that is water-impermeable according to this definition may be permeable to water vapor, i.e., may be "water vapor-permeable". Such a water vapor-permeable layer or layered structure is commonly known in the art as "breathable". As is well known in the art, a common method for measuring the permeability to water of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables and Nonwovens Association).

The terms "proximal" and "distal" refer respectively to the location of an element near to or far from the center of a structure, e.g., the proximal edge of a longitudinally extending element is located nearer to the longitudinal axis than the distal edge of the same element is located relative to the same longitudinal axis.

The terms "interior" and "exterior" refer respectively to the location of an element that is intended to be placed against or toward the body of a wearer when an absorbent article is worn and the location of an element that is intended to be placed against or toward any clothing that is worn over the absorbent article. Synonyms for "interior" and "exterior" include, respectively, "inner" and "outer", as well as "inside" and "outside". Also, when the absorbent article is oriented such that its interior faces upward, e.g., when it is laid out in preparation for setting the wearer on top of it, synonyms include "upper" and "lower", "above" and "below", "over" and "under", and "top" and "bottom", respectively.

The term "nonwoven" refers to a sheet, web, or batt of directionally or randomly oriented fibers, made by bonding or entangling the fibers through mechanical, thermal, or chemical means. Nonwoven materials exclude paper and products which are woven, knitted, tufted, or felted by wet milling. The fibers may be man-made synthetics.

The term "abdominal stretch panel" refers to a structural component that resists elongation by providing a circumferential contractive force around the waist opening of a diaper when it is stretched in the circumferential direction.

The term "application force" is the force required to extend the waist region of the diaper in order to apply the diaper onto the wearer.

The term "sustained fit force" is the force delivered by the diaper at the waist that provides the requisite body contact post application in order to deliver proper fit, gasketing, and sustained position (i.e., sustained fit).

Description of Exemplary Diaper Embodiment

In FIG. 1, FIG. 2, FIG. 3, FIG. 4, FIG. 5, and FIG. 6, the exemplary diaper 20 is shown in its flat uncontracted state prior to being formed into a pant. The finished pant product is shown in FIG. 7, FIG. 8, and FIG. 9.

One end portion of the exemplary diaper 20 may be configured as a front waist region 36. The longitudinally opposing end portion may be configured as a back waist region 38. An intermediate portion of the diaper 20 extending longitudinally between the front waist region 36 and the back waist region 38 may be configured as a crotch region 37.

The basic structure of the diaper 20 includes a chassis 100. The chassis 100 has a laterally extending front waist edge 136 in the front waist region 36 and a longitudinally opposing and laterally extending back waist edge 138 in the back waist region 38. The chassis 100 has a longitudinally extending left side edge 137a and a laterally opposing and longitudinally extending right side edge 137b, both chassis side edges extending longitudinally between the front waist edge 136 and the back waist edge 138. The chassis 100 has an interior surface 102 and an exterior surface 104. The chassis 100 also has a longitudinal axis 42 and a lateral axis 44. The longitudinal axis 42 extends through the midpoint of the front waist edge 136 and through the midpoint of the back waist edge 138. The lateral axis 44 extends through the midpoint of the left side edge 137a and through the midpoint of the right side edge 137b. The exemplary chassis 100 shown in FIG. 1 additionally has longitudinally extending and laterally opposing side flaps 147a and 147b that are described in more detail below. The portion of the chassis forming the backsheet and side flaps (including the side barriers and cuff flaps) may be formed by a web (herein, the "chassis web") comprising one or more layers. One or more of the layers forming the chassis web 149 may be water impervious. The layers forming the chassis web 149 may have different lateral extents or may be coterminus in width. And, the chassis web 149, as well as the layer or layers forming the chassis web 149, may be laterally and/or longitudinally continuous.

The basic structure of the diaper 20 also includes an absorbent assembly 200 that may be attached to the chassis 100. The absorbent assembly 200 has a laterally extending front edge 236 in the front waist region 36 and a longitudinally opposing and laterally extending back edge 238 in the back waist region 38. The absorbent assembly 200 has a longitudinally extending left side edge 237a and a laterally opposing and longitudinally extending right side edge 237b, both absorbent assembly side edges extending longitudinally between the front edge 236 and the back edge 238. The absorbent assembly 200 has an interior surface 202 and an exterior surface 204. The absorbent assembly 200 may be disposed symmetrically with respect to either or both of the longitudinal axis 42 and the lateral axis 44. Alternatively, the absorbent assembly 200 may be disposed asymmetrically with respect to either or both of the longitudinal axis 42 and the lateral axis 44. For example, the absorbent assembly 200 shown in FIG. 1 is disposed symmetrically with respect to the longitudinal axis 42 and asymmetrically with respect to the lateral axis 44. In particular, the absorbent assembly 200 shown in FIG. 1 is disposed asymmetrically toward the front waist region 36.

The respective front edge 236, back edge 238, left side edge 237a, and right side edge 237b of the absorbent assembly 200 may lie inward of the respective front waist edge 136, back waist edge 138, left side edge 137a, and right side edge 137b of the chassis 100, as in the exemplary diaper 20 shown in FIG. 1. In certain embodiments, the front edge 236 and back edge 238 of the absorbent assembly 200 may lie inward of the front and back interior abdominal stretch panels 370 and 390, e.g., between the proximal edges 372 and 392 of the interior abdominal stretch panels 370 and 390 and the lateral axis 44. Alternatively, one or more of the edges of the absorbent assembly 200 may coincide with the corresponding edge(s) of the chassis 100. In yet another alternative embodiment, as shown in FIGS. 1 and 24, the interior front and back abdominal stretch panels 370 and 390 may overlap a portion of the absorbent assembly 200. In such an overlapping configuration, it may be advantageous for the interior abdominal stretch panels 370 and/or 390 to remain unattached to the absorbent assembly 200 over a portion of the longitudinal extent of the abdominal stretch panel 370 and/or 390, particularly in the laterally central portions of the chassis, i.e., area between the laterally opposing side flaps 147, for example 117 and 118, to provide an abdominal stretch panel waist cap or stand up waist feature forming a pocket 650 which helps to prevent leakage of urine and/or feces at the waist.

The chassis 100 and 100 may additionally include an inner liner 22 attached to the backsheet 26 and/or the absorbent assembly 200 as illustrated in FIGS. 16 and 17. The inner liner 22 may form a portion of the interior surface 102 of the chassis 100 that is intended to be placed against the body of the wearer. The inner liner 22 may be formed of a soft material that will not irritate the skin of the wearer. Such an inner liner 22 may serve to isolate the skin of the wearer from a portion of the backsheet 26 as may be desirable, for example, when the diaper 20 is worn under conditions in which contact between the skin and a backsheet 26 could be uncomfortable. Many suitable materials for the inner liner 22 are well-known in the art, including rayon and synthetic nonwovens such as spunbonded or carded polypropylene or polyester. The inner liner 22 may extend to the same width and the same length as the backsheet 26.

Alternatively, one or more of the edges of the inner liner 22 may lie inward of the edges (i.e., side edges 137a and b, and waist end edges 136 and 138) of the chassis 100. For example, with reference to the exemplary diaper 20 shown in FIG. 1 only the portions of the inner liner 22 (see FIGS. 16 and 17) lying in a front gap 606 between the front edge 236 of the absorbent assembly 200 and the front waist edge 136 of the chassis 100 and a back gap 607 between the back edge 238 of the absorbent assembly 200 and the back waist edge 138 of the chassis 100 are exposed, while the remainder of the inner liner 22 is covered by the absorbent assembly 200 and the side flaps 147a and b. Therefore, a laterally extending strip of the inner liner 22 disposed in the front gap 606 in the front waist region 36 and a similar laterally extending strip of the inner liner 22 disposed in the back gap 607 in the back waist region 38 may suffice to isolate the skin of the wearer from the backsheet 26 in these two gaps. The inner liner 22 may be partially disposed under the side flaps 147 or alternatively the inner liner 22 may be disposed on top of the side flaps 147 in one or both of the waist regions 36 and 38. In certain embodiments, as shown in FIG. 25, the inner liner 22 may overlap a portion of the absorbent assembly 200. In such an overlapping configuration, it may be advantageous for the inner liner 22 to remain unattached to the absorbent assembly 200 over a portion of the longitudinal extent of the inner liner 22 particularly in the laterally central portions, area between the laterally opposing side flaps 147, for example 117 and 118, to provide an inner liner waist cap or stand up waist feature forming a pocket 650 which helps to prevent leakage of urine and/or feces at the waist.

The basic structure of the diaper 20 also includes at least one abdominal stretch panel that may be attached to the chassis 100 in a waist region. When the chassis 100 is stretched in the circumferential direction, the abdominal stretch panel resists by providing a circumferential contractive force around the waist opening of the diaper 20. In FIG. 1, FIG. 2, FIG. 3, FIG. 4, FIG. 5, and FIG. 6, the diaper 20 is shown as having four abdominal stretch panels. In particular, in FIG. 1 and FIG. 3, a front interior abdominal stretch panel 370 is shown attached interiorly to the chassis 100 in the front waist region 36 of the diaper 20. Similarly, in FIG. 1 and FIG. 6, a back interior abdominal stretch panel 390 is shown attached interiorly to the chassis 100 in the back waist region 38 of the diaper 20. In FIG. 2 and FIG. 3, a front exterior abdominal stretch panel 360 is shown attached exteriorly to the chassis 100 in the front waist region 36. Finally, in FIG. 2 and FIG. 6, a back exterior abdominal stretch panel 380 is shown attached exteriorly to the chassis 100 in the back waist region 38 of the diaper 20. The abdominal stretch panel may be applied to the surface of the absorbent article in an untensioned state, i.e. the abdominal stretch panel applies little or no contractive force on the article until the waist region of the article is extended laterally, e.g. during application. Alternatively, the abdominal stretch panel may be applied to the surface of the absorbent article under tension and therefore applies some contractive force to the waist region of the article prior to use.

Alternatively, the diaper 20 may have four abdominal stretch panels as described above, or may have only one, two, or three abdominal stretch panels, as desired for providing an appropriate level of circumferential contractive forces around the waist of a wearer. For example, in some embodiments, the diaper 20 may have only a front exterior abdominal stretch panel 360, while in other exemplary embodiments, the diaper 20 may have both a front exterior abdominal stretch panel 360 and a back exterior abdominal stretch panel 380. In some exemplary embodiments, the diaper 20 may have only a front interior abdominal stretch panel 370, while in other exemplary embodiments, the diaper 20 may have both a front interior abdominal stretch panel 370 and a back interior abdominal stretch panel 390. In some exemplary embodiments, the diaper 20 may have an exterior abdominal stretch panel and an interior abdominal stretch panel in either the front waist region 36 or the back waist region 38, and only either an exterior abdominal stretch panel or an interior abdominal stretch panel in the opposing waist region. The exterior abdominal stretch panels 360 and 380 may be attached to the exterior surface of the backsheet 26. The interior abdominal stretch panels 370 and 390 may be attached to the interior surface of the chassis 102 and/or the interior surface of the absorbent assembly 202 and/or the upper surfaces 613a and b of the side flaps 147a and b.

During application of the diaper 20, particularly a diaper configured as a pull-on pant, the diaper 20 may be pulled upward along the legs and over the hips of the wearer to the waist. Several factors impact ease of application for pull-on style diapers. First, the wearer or caregiver should be able to get the wearer's legs through the leg openings easily. Second, the abdominal stretch panels 360, 370, 380, and 390 should have an acceptable application force (i.e., the force that allows a wearer or caregiver of the wearer to extend the abdominal stretch panels 360, 370, 380, and 390 and pull the diaper upward over the wearer's buttocks and hips without excessive effort). Excessive application force makes application of the diaper 20 more difficult for both the caregiver and/or the wearer, for example a potty training child who pulls the pant up and down on their own. Finally, the abdominal stretch panels 360, 370, 380, and 390 should provide an adequate level of wearing force or sustained fit force (i.e., the force that the abdominal stretch panels 360, 370, 380, and 390 apply to the waist of the wearer during wear providing the requisite sustained fit, including maintaining the position, fit, and gasketing of the diaper 20 at the waist, without marking the skin).

As shown in FIG. 7, FIG. 8, and FIG. 9, when the diaper 20 is worn on the lower torso of a wearer, the front waist edge 136 and the back waist edge 138 of the chassis 100 encircle the waist of the wearer, while at the same time the chassis side edges 137a and 137b encircle the legs of the wearer. At the same time, the crotch region 37 may be positioned between the legs of the wearer and the absorbent assembly 200 extends from the front waist region 36 through the crotch region 37 to the back waist region 38.

Description of the Chassis

The chassis 100 includes a water-impermeable backsheet 26. The backsheet 26 forms an exterior surface that is intended to be placed toward any clothing that is worn over the diaper 20. Many suitable materials for use as the backsheet 26 are well-known, including films of polyethylene and other polyolefins. Multi-layer backsheets, such as a laminate of a film 30 and a nonwoven material 31 or a laminate of multiple nonwoven layers, may also be suitable for use as the backsheet 26. Such a backsheet may be oriented with the nonwoven 31 disposed exteriorly of the film, as shown in FIG. 1, FIG. 2, FIG. 3, FIG. 4, FIG. 5, and FIG. 6, to provide the feel and appearance of a more cloth-like outermost layer than would be provided by using the film 30 as the outermost layer. A multi-layer backsheet 26, such as a laminate of a film 30 and a nonwoven 31, may also be suitable for use with the nonwoven 31 disposed interiorly to separate the film 30 from the skin of the wearer, or with nonwoven 31 disposed both exteriorly and interiorly, such that the film 30 is sandwiched. In addition, the nonwoven 31 and film 30 layers of the multi-layer laminate may have different widths, for example the film 30 may be wider than the nonwoven 31 or alternatively the nonwoven 31 may be wider than the film 30.

As shown in FIG. 1, FIG. 2, FIG. 3, FIG. 4, FIG. 5, and FIG. 6, the exemplary chassis 100 has longitudinally extending and laterally opposing side flaps 147 that are disposed on the interior portion of the diaper 20 that faces inwardly toward the wearer and contacts the wearer. The side flaps 147 may be formed by folding portions of the chassis 100 laterally inward, i.e., toward the longitudinal axis 42, to form both the respective side flaps 147 and the side edges 137 of the chassis 100. Alternatively, as shown in FIG. 23, the side flaps 147 may be formed by attaching an additional layer or layers to the chassis 100 at or adjacent to each of the respective side edges 137 of the chassis 100.

Each side flap 147 has a proximal edge 157. In the exemplary diaper 20 shown in FIG. 1, the side flaps 147 overlap the absorbent assembly 200, i.e., the proximal edges 157 lie laterally inward of the respective side edges 237 of the absorbent assembly 200. Such an overlapped configuration may be desirable in order to impart a more finished appearance to the diaper 20 than that imparted by a non-overlapped configuration. Alternatively, the side flaps 147 may not overlap the absorbent assembly 200.

Each of the side flaps 147 may be attached to the interior surface 102 of the chassis 100 in longitudinally oriented side flap attachment zones 151 in the front waist region 36 and longitudinally oriented side flap attachment zones 152 in the back waist region 38.

In the exemplary chassis 100 shown in FIG. 1, the side flaps 147 may also be attached to the interior surface 102 of the chassis 100 in laterally oriented side flap attachment zones 153 adjacent to the front waist edge 136 and in a longitudinally opposing laterally oriented side flap attachment zones 154 adjacent to the back waist edge 138.

In embodiments in which the front edge 236 or the back edge 238 of the absorbent assembly 200 coincides with the respective front waist edge 136 or back waist edge 138 of the chassis 100 and the side flaps 147 overlap the absorbent assembly 200, the side flaps 147 may be attached to the absorbent assembly 200 instead of, or in addition to, being attached to the interior surface 102 of the chassis 100.

In embodiments in which the chassis 100 comprises a multi-layer chassis web 149, such as a laminate of a film 30 and a nonwoven 31, the nonwoven 31 may extend laterally to the full extent, width of the film 30 or alternatively the nonwoven 31 may have a width that is less than or greater than that of the film 30 layer. In an embodiment where the nonwoven 31 has a width, lateral extent, that is less than that of the film 30, the portion of the chassis web 149 that is folded to form the side flap 147 may consist solely of the film 30 layer, or may consist substantially of the film 30 layer (in other words, for a multilayered chassis web 149, the nonwoven 31 may extend across the exterior surface 104 from one chassis side edge 137a to the opposing side edge 137b; or alternatively, the nonwoven 31 may wrap the chassis side edges 137a and b and cover a portion of the side flaps 147a and b). In an embodiment where the nonwoven 31 has a width, lateral extent, that is greater than that of the film 30, the portion of the chassis web 149 that is folded to form the side flap 147 may consist solely of the nonwoven 31 layer, or may consist substantially of the nonwoven 31 layer. Furthermore, the nonwoven 31 of a multi-layer chassis web 149 may extend longitudinally to the full extent, length, of the film 30 or alternatively the nonwoven 31 may have a longitudinal extent that is less than that of the film 30 layer. In an embodiment where the nonwoven 31 has a length, longitudinal extent, that is less than that of the film 30, the portion of the chassis 100 uncovered by the nonwoven 31 in the front and/or back waist regions 36 and 38 may be covered by the abdominal stretch panels 360, 370, 380, and 390.

Between the longitudinally opposing side flap attachment zones, the proximal edges 157 of the side flaps 147 remain free, i.e., are not attached to the interior surface 102 of the chassis 100 or to the absorbent assembly 200. Also between the longitudinally opposing side flap attachment zones, each side flap may include one or more (specifically including one, two, three, or four strands per side flap) longitudinally extensible flap elastic gathering members that may be attached adjacent to the proximal edge of the side flap by any of many well-known means. Each of such flap elastic gathering members may be attached over its entire length or over only a portion of its length. For example, such flap elastic gathering members may be attached only at or near its longitudinally opposing ends and may be unattached at the middle of its length. Such flap elastic gathering members may be disposed in the crotch region 37 and may extend into one or both of the front waist region 36 and the back waist region 38. For example, in the exemplary chassis 100 shown in FIG. 1, an elastic strand 167 may be attached adjacent to the proximal edge 157 of each of the side flaps 147 and extends into both the front waist region 36 and the back waist region 38.

Each flap elastic gathering member may be enclosed inside a folded hem. For example, in the exemplary chassis 100 shown in FIG. 4 and FIG. 5, each of the elastic strands 167 may be enclosed inside a hem 170 formed adjacent to the proximal edge 157 of the respective side flap 147. Alternatively, the flap elastic gathering member(s) may be sandwiched between two layers of the chassis or may be attached on a surface of the chassis 100 and remain exposed.

When stretched, the flap elastic gathering member disposed adjacent to each side flap proximal edge allows the side flap edge to extend to the flat uncontracted length of the chassis, e.g., the length of the chassis 100, as shown in FIG. 1. When allowed to relax, the flap elastic gathering member contracts to pull the front waist region 36 and the back waist region 38 toward each other and thereby bend the diaper 20 into a "U" shape in which the interior of the "U" shape may be formed by the portions of the diaper 20 that are intended to be placed toward the body of the wearer. Because each of the proximal edges 157 remains free between the longitudinally oriented side flap attachment zones 151 and 152, the contractive force of the elastic strand 167 lifts the proximal edge 157 of the side flap 147 away from the interior surface 102 of the chassis 100. This lifting of the proximal edges 157 when the diaper 20 is in the relaxed condition lifts the side flaps 147 into position to serve as side barriers adjacent to the side edges 237 of the absorbent assembly 200.

As shown in FIGS. 1, 2, 4, 5, 18, 19, and 20, one or more (specifically including one, two, three, or four strands per side flap) second elastic strands 168a and b may be attached at or adjacent the chassis side edges 137a and b of the chassis 100 where it is folded to form the side flaps 147a and b. When allowed to relax, the second elastic strands 168a and b may gather the side edges 137a and b of the chassis 100 to form side barriers 633a and b and function as a barrier to leakage of urine and fecal waste. A channel 621a and b may be formed adjacent the side edge 137a and b of the chassis 100 where it is folded to form the side flap 147a and b such that the portion of the chassis web 149 forming the channel 621a and b remains largely non-adhered to itself or to the second elastic strands 168a or b, particularly in each of the opposing waist regions 36 and 38, such that the second elastic strands 168a and b floats in the hollow of the channels 621a and b to enable the second elastic strands 168a and b to snap back to its glued-in length once the diaper 20 is cut to length during manufacture.

As shown in FIGS. 2, 4, 5, 18, 19 and 20 the side flaps 147 may be formed into cuff flaps 631 and side barriers 633. Particularly, side barrier attachments 630 may be oriented between the first and second elastic strands 167 and 168. The placement of side barrier attachments 630 relative to the longitudinal axis 42 has a direct and coupled effect on the depth of cuff flaps 631 and the size of the side barriers 633. For example, when the side barrier attachments 630 are moved laterally inward, the depth of the cuff flaps 631 decreases and the size of the side barriers 633 increases. Conversely, as shown in FIG. 18, when the side barrier attachments 630 are moved laterally outward, the depth of the cuff flaps 631 increases and the size of the side barriers 633 decreases. The depth and/or size of the cuff flaps 631 and side barriers 633 may be adjusted for various applications to provide enhanced functionality. In one such embodiment, as shown in FIG. 19, it has been found that reduced depth cuff flaps 631 and larger side barriers 633 provides better application ease with regard to a pull-on pant style application. This configuration increases the size of the leg opening (not shown in FIG. 19) enabling the wearer to step into the diaper 20 more easily. In yet another embodiment, it has been found that increasing the depth of the cuff flaps 631 and reducing the size of the side barriers 633 provides improved leakage protection and increased perception of capacity.

The depth of the cuff flaps 631 as measured from the proximal edge 157 of the side flap 147 to the side barrier attachment 630 may be from about 2 cm to about 7 cm, from about 2.5 cm to about 6.5 cm, or from about 3 cm to about 6 cm. The length of the side flap 147, as measured from the proximal edge 157 of the side flap 147 to the side edge 137 of the chassis 100 may be from about 4.5 cm to about 9.5 cm, from about 5 cm to about 8.5 cm, or from about 5.5 cm to about 7.5 cm. Alternatively, as shown in FIG. 20, a second pair of side barrier attachments 630c and d may be used such that one can adjust the height of the cuff flaps 631 of the side flaps 147 without impacting the height of the side barriers 633. A channel 634a and b may be formed between side barrier attachments 630a and c and/or 630b and d and may comprise one or more additional elastic gathering members/strands 635a and b disposed therein.

For embodiments wherein the side flaps 147 are formed by attaching additional layers (e.g., film 30 and/or nonwoven 31) to the chassis 100 at or adjacent to each of the respective side edges 137a and b of the chassis 100, the second elastic strand 168a and b may be oriented and attached between the layers (e.g., film 30 and nonwoven 31) see FIG. 24. The layers (e.g., film 30 and nonwoven 31) may also form a channel (e.g., 621a and b) and provide the functionality associated with it as described above.

At and/or adjacent to each of the side edges 137 of the chassis, the front waist region 36 and the back waist region 38 are attached together to form the finished pant product having a waist opening 10 and two leg openings 12. This attachment may have the form of side seams 115. Such a side seam may be formed where the waist regions are overlapped such that the interior surface of one lies against the exterior surface of the other. In another form, a side seam may be formed where the side edges in the waist regions are abutted. In another form, a side seam may be formed where either the interior surfaces or the exterior surfaces of the waist regions are in face-to-face contact, i.e., in a so-called flanged attachment. Such flanged attachments are shown in FIG. 7, FIG. 8, and FIG. 9.

Referring to FIG. 7, side seam 115 may comprise primary closure members 700 which are refastenable. The primary closure members 700 may comprise any refastenable fastening components known in the art. For example, the primary closure members 700 may comprise mechanical fasteners, e.g. hook and loop fasteners, hook and hook fasteners, macrofasteners, buttons, snaps, tab and slot fasteners, tape fasteners, adhesive fasteners, cohesive fasteners, magnetic fasteners, hermaphrodidic fasteners and the like. Some suitable examples of fastening systems and/or fastening elements are discussed in U.S. Pat. Nos. 3,848,594; 4,662,875; 4,846,815; 4,894,060; 4,946,527; 5,151,092; 5,221,274; 6,251,097; 6,669,618; and 6,432,098; U.S. patent application Ser. No. 11/240,943, entitled, "Anti-Pop Open Macrofasteners" filed on Sep. 30, 2005; and Ser. No. 11/240,838, entitled, "A Fastening System Having Multiple Engagement Orientations", filed on Sep. 30, 2005. Additionally, various suitable pant configurations are disclosed in U.S. Pat. Nos. 5,246,433; 5,569,234; 6,120,487; 6,120,489; 4,940,464; 5,092,861; 5,897,545; 5,957,908; and U.S. Patent Publication Nos. 2003/0233082; 2005/0234419A1; 2003/0088220; 2005/0130821; 2003/0233082; 2005/0215971; 2005/0215970; 2007/0078427; 2007/0093769; 2007/0074381; 2007/0078426A1; and 2008-0107861.

A side seam may be formed where the waist regions are overlapped such that the interior surface of one lies against the exterior surface of the other. In such an embodiment, one closure member 700 may be disposed on the interior surface of the side flap while the other closure member 700 is disposed on the exterior surface of the backsheet. In an alternative embodiment, a side seam may be formed where the side edges in the waist regions are abutted. In such an embodiment, the closure member 700 may be disposed on the outer surface of the backsheet in both the front and back waist regions and/or on the inner surface of the side flaps in the front and back waist regions such that it spans from one waist region to the opposing waist region. In yet another embodiment, a side seam may be formed where either the interior surfaces or the exterior surfaces of the waist regions are in face-to-face contact, i.e., in a so-called flanged attachment. Such flanged attachments are shown in FIG. 7, FIG. 8, and FIG. 9.

In other embodiments, secondary closure members (not shown) may be employed to enable adjustment of the article once the article has been applied to a wearer. Secondary closure members (not shown) serve to increase the tension (i.e., "cinch") in the waist hoop subsequent to application in order to provide enhanced sustained fit of the article. Secondary closure members (not shown) may include any type of fastener as known in the art and may be associated with a stretch element that aids in increasing the tension in the waist hoop. A secondary closure member (not shown) may be disposed adjacent one of the primary closure members 700 or may be made unitarily with one of the primary closure members 700, The purpose of a secondary closure member (not shown) is to allow the user to adjust the fit of the article. It should be understood that multiple closure members, i.e. primary, secondary, tertiary, etc. may be incorporated into one or all of the components forming the refastenable side seam 115.

Further, it should be appreciated that closure members 700 need not have an infinite life span, but it is sufficient that the closure members 700 attached in a refastenable manner can be separated and re-attached successively several times over the typical use life span of the absorbent article. It will also be appreciated that the aggressiveness of actual fastening may be reduced significantly from fastening to refastening in absolute terms, but that such reduction is not "substantial degradation" of fastener performance if the resulting refastened strength is sufficient for the fastening system's purpose of use.

A portion or the whole of the chassis 100 may be made extensible to a degree greater than the inherent extensibility of the material or materials from which the chassis is made, e.g., the backsheet 26. The additional extensibility may be desirable in order to allow the chassis 100 to conform to the body of a wearer during movement by the wearer. The additional extensibility may also be desirable, for example, in order to allow the user of a diaper 20 including a chassis 100 having a particular size before extension to extend the front waist region 36, the back waist region 38, or both waist regions of the chassis 100 to provide additional body coverage for wearers of differing size, i.e., to tailor the diaper to the individual wearer. Such extension of the waist region or regions may give the diaper a generally hourglass shape, so long as the crotch region 37 is extended to a relatively lesser degree than the waist region or regions, and may impart a tailored appearance to the diaper 20 when it is worn. In addition, the additional extensibility may be desirable in order to minimize the cost of the diaper. For example, an amount of material that would otherwise be sufficient only to make a relatively smaller diaper lacking this extensibility can be used to make a diaper capable of being extended to adequately cover a wearer that is larger than the unextended smaller diaper would fit.

A portion of the chassis 100 in the front and/or back waist regions 36 and 38 may be made laterally extensible to a maximum extensibility greater than a maximum extensibility of another portion of the chassis 100 in the crotch region 37 such that a lateral extension of each of the portions in the front, back, and crotch regions 36, 38, and 37 to its maximum extensibility imparts an hourglass shape to the chassis 100. In one embodiment, the portion of the chassis 100 underlying and/or immediately adjacent an abdominal stretch panel (e.g., back/front interior/exterior abdominal stretch panels 360, 370, 380, and 390) may be made laterally extensible to a maximum extensibility greater than a maximum extensibility of another portion of the chassis 100, for example the crotch region 37, such that a lateral extension of each of the portions to its maximum extensibility facilitates application of the diaper 20 onto the body of a wearer by enabling the waist opening 10 to be extended to fit over the wearer's hips and in addition, opening and orienting the leg openings 12 enabling the wearer to place the legs through the leg openings 12 more effectively.

Additional lateral extensibility in the chassis 100 may be provided in a variety of ways. For example, a material or materials from which the chassis 100 is made may be pleated by any of many known methods. Alternatively, all or a portion of the chassis may be intermittently activated to create a structured elastic-like formed web material or a formed laminate of web materials like those described in U.S. Pat. No. 5,518,801 issued on 21 May 1996 in the name of Chappell et al. This formed web material includes distinct laterally extending regions in which the original material has been altered by embossing or another method of deformation to create a pattern of generally longitudinally oriented alternating ridges and valleys and also includes laterally extending unaltered regions between the laterally extending altered regions. The formed web material can be extended in a direction perpendicular to the ridges up to the point where the ridges and valleys flatten with substantially less force than is required to extend beyond that point. In addition to lateral extensibility, the creation of a formed laminate web as described above provides the backsheet 26 with improved texture and cloth-like appearance and feel. The deformation creates a cloth-like pattern in the film and increases the loft of the nonwoven 31 in multi-layer film 30 and nonwoven 31 laminate backsheets 26.

An exemplary fragment 300 of such a formed web material 305 is shown in FIG. 27. This formed web material 305 includes distinct laterally extending regions 310 in which the original material has been altered by embossing or another method of deformation to create a pattern of generally longitudinally oriented alternating ridges 312 and valleys 314. The formed web material 305 also includes laterally extending unaltered regions 316 located between the laterally extending altered regions 310.

Such a formed web material 305 can be laterally extended beyond its original dimension with the application of relatively less force than that required to extend the same material to the same extent when undeformed. In particular, the effects of an application of opposing divergent forces directed generally perpendicular to the ridges 312 and valleys 314 include an extension of such a formed web material along an axis between the opposing forces and the generation of a resistive contractive force, primarily in the unaltered regions 316. This resistive force is relatively smaller than the resistive force that is generated by the same material in its unaltered form when extended to the same extent, at least up to an extension at which the ridges and valleys in the altered regions flatten and begin to contribute to the resistive force. Thus, such formed web materials exhibit an extensible behavior resembling that of traditional elastic materials in the range of extensibility that is useful for the type of lateral extension desired for use in absorbent articles. However, such formed web materials may be made of relatively less expensive materials that are not inherently elastic and, thus, their use may provide an advantage in terms of the cost of manufacturing the absorbent articles.

Alternatively, a portion of the chassis can be continuously activated (e.g., ring-rolled and thus rendered highly extensible as described in U.S. Pat. No. 5,366,782 (issued Nov. 22, 1994 to Curro, et al)). Specifically, a ring-rolling apparatus (not shown), which comprises opposing rolls (not shown) having intermeshing teeth (not shown) that incrementally stretch and thereby plastically deform the chassis (or a portion thereof) thereby rendering the chassis extensible in the ring-rolled regions. In one embodiment, the backsheet 26 can be ring-rolled in a portion of at least one of the front or back waist regions 36 and 38, for example the portion of the chassis 100 underlying and/or immediately adjacent the back/front interior/exterior abdominal stretch panels 360, 370, 380, and 390, while other regions may comprise a structured elastic-like formed web material.

The activation approaches described above are achieved by using a set of opposing rolls comprising a staggered orientation of teeth such that when a material such as the chassis web 149 or backsheet passes through the intermeshing rolls, the material is deformed to create the desired activation pattern in the web. Alternatively, the teeth of one of the rolls may be continuous around the circumference of the roll while the teeth on the opposing roll may be discontinuous forming intermittent activation (e.g. a structured elastic-like formed web) or a pitched continuous activation (e.g. continuously activated in the opposing waist regions and not the crotch region). The depth to which the teeth intermesh, i.e. depth of engagement, will determine to what degree the web is incrementally stretched and/or plastically deformed and therefore the degree of extensibility imparted to the web.

In some embodiments, the chassis web 149 can be activated in a portion of side barriers or cuff flaps to a greater extent, for example, length of the activated/deformed region or the depth of engagement. For example, in these embodiments, one or both of the waist regions of the chassis immediately adjacent the side edges may comprise longer longitudinally oriented ridges and valleys while other portions of the waist region may comprise relatively shorted longitudinally oriented ridges and valleys. Alternatively, one or both of the waist regions of the chassis immediately adjacent the side edges and or end edges may comprise a material that has been deformed to a greater extent forming larger (i.e. deeper) longitudinally oriented ridges and valleys while other portions of the absorbent article may comprise relatively smaller (i.e. shallower) longitudinally oriented ridges and valleys.

In certain embodiments, the activated portion of the chassis web 149 disposed in one of the front or back waist region may comprise a continuous activation pattern (e.g., via ring rolling) and an intermittent activation pattern (i.e., a structured elastic-like formed web material). These two activation patterns may be disposed in an overlapping or side-by-side relationship. For example, as a more particular embodiment, the entire chassis web 149 may be intermittently activated to form a structured elastic-like formed web material and the portion of the chassis web 149 disposed in one or both of the waist regions may be continuously activated, such that the continuously activated region overlaps the intermittently activated region.

As illustrated in FIG. 26, when exterior abdominal stretch panels 360 and 380 are used, but not interior abdominal stretch panels 370 and 390, ring-roll type (e.g. continuous) activation may create corrugations 636 in the interior of the waist regions 36 and 38. Specifically, the chassis 100 (including the backsheet 26, side flaps 147, and inner liner 22 (when present)), may be corrugated to provide an undulating inner surface 102, forming the corrugations 636. These corrugations 636 are believed to promote breathability and, overall, a healthier environment for the wearer's skin, particularly in the waist region.

Alternatively, when interior abdominal stretch panels 370 and 390 are used, but not exterior abdominal stretch panels 360 and 380, ring-roll type (e.g. continuous) activation may create corrugations 636 on the exterior of the waist regions 36 and 38. Specifically, the chassis 100 (including the backsheet 26, side flaps 147, and inner liner 22 (when present)), may be corrugated to provide an undulating outer surface 104, forming the corrugations 636. These corrugations 636 are believed to provide an impression of extensibility as the waist region of the article is extended during application.

The chassis 100 may be ring-rolled across the entire width in one or both of the front/back waist regions 36 and 38 or alternatively may be ring-rolled over only a portion of the chassis 100 width. In yet another embodiment the portion of the chassis 100 may be ring-rolled where the side flaps 147a and b overlap and are joined to the chassis 100 in the side flap attachment zones 151, 152, 153, and 154. The ring-rolling may take place prior to folding portions of the chassis 100 to form the side flaps 147a and b or alternatively after the side flaps 147a and b have been formed and/or attached. Further, ring-rolling may take place after the back/front interior/exterior abdominal stretch panels 360, 370, 380, and 390 are attached.

The front laterally central portion 117 and the back laterally central portion 118 of the chassis 100 may have a different range of extensibility from the portions of the chassis in the side flap attachment zones 151, 152, 153, and 154 where the side flaps 147a and 147b may be attached to the interior surface 102 of the chassis. Additionally or alternatively, the laterally central portions 117 and 118 may be extensible to a greater or lesser degree when subjected to a given level of opposing tensile forces, i.e., may be more easily or less easily extensible, than the portions of the chassis in the side flap attachment zones. For example, if the chassis is made uniformly extensible across its entire width prior to the formation of the side flaps, the double layering in the areas of the side flap attachment zones after the formation of the side flaps may have an effect of decreasing the degree of lateral extensibility of those areas under a given level of opposing tensile forces, such as by the side flaps acting as parallel "springs" that may be extended in order to extend the underlying attached portion of the chassis. As another example, the altered regions in the laterally central portions of the chassis may be deformed to a greater or a lesser degree than the altered regions in the side flap attachment zones to render the laterally central portions more easily or less easily extensible than the respective portions in the side flap attachment zones.

Description of the Abdominal Stretch Panels

As shown in the figures, each abdominal stretch panel has a circumferentially extending longitudinally distal edge that is disposed at or adjacent to the respective waist edge of the chassis 100 and a longitudinally opposing circumferentially extending longitudinally proximal edge that is disposed relatively nearer to the lateral axis 44 than the longitudinally distal edge of the same abdominal stretch panel is disposed. As shown in FIGS. 10 and 11, each abdominal stretch panel also has laterally opposing longitudinally extending side edges 373, an interior surface 374, and an exterior surface 375.

In particular, the front interior abdominal stretch panel 370, when present, has a circumferentially extending longitudinally distal edge 371 and a longitudinally opposing circumferentially extending longitudinally proximal edge 372. The front interior abdominal stretch panel 370, when present, also has laterally opposing longitudinally extending side edges 373, an interior surface 374, and an exterior surface 375. Similarly, when present, the back interior abdominal stretch panel 390 has a distal edge 391, a proximal edge 392, side edges 393, an interior surface 394, and an exterior surface 395. Similarly, when present, the front exterior abdominal stretch panel 360 has a distal edge 361, a proximal edge 362, side edges 363, an interior surface 364, and an exterior surface 365. Similarly, when present, the back exterior abdominal stretch panel 380 has a distal edge 381, a proximal edge 382, side edges 383, an interior surface 384, and an exterior surface 385.

Each of the abdominal stretch panels shown in FIG. 1, FIG. 2, FIG. 3, and FIG. 6 has a circumferential extent that is substantially equivalent to the lateral extent of the chassis 100 in the respective waist region. In such embodiments, each abdominal stretch panel may be attached to the chassis 100 where the front waist region 36 and the back waist region 38 are attached together. For example, if a side seam 115 is formed by means of pressure bonding or thermal bonding in any of their forms, including ultrasonic bonding, an abdominal stretch panel may be attached to the chassis in the same side seam, such that the side seam effectively extends through the thicknesses of the chassis 100 and the abdominal stretch panel. An ability to bond all of the layers together in one side seam may have advantages in terms of manufacturing simplicity and cost, because the side seam can be formed in a single bonding process.

The number of apertures 622 per unit area of apertured web (i.e., the area density of apertures 622) can be varied from about 1 aperture 622 per square centimeter to as high as 60 apertures 622 per square centimeter. There can be at least 10 or at least 20 apertures 622 per square centimeter, depending on the end use. In general, the area density need not be uniform across the entire area of web, but apertures 622 may be oriented in only certain regions (e.g., the front or back waist regions 36 and 38) of the chassis 100, and can be disposed in a variety of shapes, including lines, stripes, bands, circles, and the like.

The abdominal stretch panels attached to the chassis as described herein are desirable from the standpoints of comfort and appearance. For example, unlike typical stretch waistbands, each abdominal stretch panel covers some portion of a waist region of the diaper 20, i.e., is disposed on one or both of the interior and exterior surfaces rather than being hidden between layers of the chassis 100. Therefore, if the abdominal stretch panel is formed from soft and attractive materials, such as one of the aforementioned nonwovens, the exposed abdominal stretch panel can provide a finished appearance resembling that of cloth underwear and thereby convey an impression of softness and comfort to the user.

Description of the Absorbent Assembly

As shown in FIGS. 12, 13, 14, and 15, the absorbent assembly 200 includes an absorbent core 250 that serves to absorb and retain liquid bodily waste materials. The absorbent core 250 has a laterally extending front edge 256 and a longitudinally opposing and laterally extending back edge 258. The absorbent core 250 also has a longitudinally extending left side edge 257*a* and a laterally opposing and longitudinally extending right side edge 257*b*, both absorbent core side edges extending longitudinally between the front edge 256 and the back edge 258. The absorbent core 250 also has an interior surface 252 and an exterior surface 254.

The absorbent assembly 200 may be attached to the interior surface 102 of the chassis 100 over any part or the whole of the area of the absorbent assembly 200. The absorbent assembly 200 may be attached on its exterior surface 204 to the chassis 100 in a shaped attachment pattern, for example a cruciform attachment pattern, i.e., an attachment pattern that forms or is arranged in a cross or "+" shape.

Suitable configurations of cruciform attachment patterns are disclosed in U.S. Pat. No. 6,962,578 to La Von issued on 8 Nov. 2005.

Alternatively, the absorbent assembly 200 may be attached to the interior surface 102 of the chassis 100 in a convexly-shaped attachment pattern 210', which may be in the shape of an oval or may be egg-shaped. The convexly-shaped attachment pattern 210' may be contiguous, i.e., all of its portions may be touching or connected throughout the pattern in an unbroken sequence. Alternatively, it may include detached portions and thereby lack contiguity but still be arranged such that the shape of the overall pattern is in the form of, for example, an oval. For example, a discontiguous convexly-shaped attachment pattern 210' may include a longitudinally extending portion disposed along the longitudinal axis 42 and separate left and right laterally spaced portions disposed along or adjacent to the lateral axis 44, the laterally spaced portions having extending longitudinally to different lengths thereby forming an oval shaped pattern. In one embodiment, shown in FIG. 21, the oval-like attachment pattern 210 comprises 5 laterally spaced stripes of adhesive 624-628 attaching the absorbent assembly 200 to the interior surface 102 of the chassis 100. The central stripe 626 may be disposed at or adjacent the longitudinal axis 42 and is shown as having the greatest longitudinal extent. The most distal of the adhesive stripes 624 and 628 are shown as having the least longitudinal extent and the intermediate stripes 625 and 627, those located between the distal stripes 624 and 628 and the central stripe 626 are shown having a longitudinal extent between that of the central stripe 626 and the distal stripes 624 and 628.

The portions of the chassis 100 that lie outside such a convexly-shaped attachment pattern 210 or oval-like attachment pattern 210 are not restrained by attachment to the absorbent assembly 200 and therefore remain extensible. Thus, in embodiments where the absorbent assembly 200 is attached to the backsheet 26 in the convexly-shaped attachment pattern 210, the backsheet 26 substantially loses its extensibility in the area of attachment. The portion of the backsheet 26 disposed outside of the convexly-shaped attachment pattern 210 may remain extensible. Thus, it may be desirable to activate the backsheet 26 in a pattern complimentary with a given attachment pattern (e.g., a concave activation pattern 675 to compliment a convexly-shaped or oval-like attachment patterns 210).

Within the extent of the shaped attachment patterns (e.g., the cruciform, convexly-shaped, and oval-like attachment patterns 210), the absorbent assembly 200 may be attached to the chassis 100 continuously or intermittently as shown in FIGS. 21 and 22. For example, a film of adhesive (not shown) may be applied continuously over the entire area of the cruciform attachment pattern 210 and then used to continuously attach the absorbent assembly 200 to the chassis 100. As an alternative example, an adhesive may be applied discontinuously at and inside the boundaries of the convexly shaped attachment pattern 210", such as in the form of dots, stripes (e.g., stripes 624-628), beads, spirals, etc., and then used to attach the absorbent assembly 200 to the chassis 100.

The shaped attachment patterns (e.g., the cruciform, convexly-shaped, and oval-like attachment patterns 210) may be disposed symmetrically or asymmetrically with respect to either or both of the longitudinal axis 42 and the lateral axis 44 of the chassis 100. In addition, the shaped attachment patterns (e.g., the cruciform, convexly-shaped, and oval-like attachment patterns 210) may be disposed symmetrically or asymmetrically with respect to either or both of the side edges 237*a* and *b* and the front and back edges 236 and 238 of the absorbent assembly 200. Other suitable configurations of cruciform attachment patterns 210 are disclosed in U.S. Pat. No. 6,962,578 issued on 8 Nov. 2005.

The absorbent core 250 may be disposed between a lower covering sheet that is disposed on the exterior face of the absorbent core 250 and an upper covering sheet that is disposed on the interior face of the absorbent core 250. Such an upper covering sheet and lower covering sheet may be attached together to contain the absorbent core 250 between them and thereby form the absorbent assembly 200. For example, in the exemplary absorbent assembly 200 shown in FIGS. 12, 13, 14 and 15, an upper covering sheet 24 and a lower covering sheet 25 are attached together at or adjacent to the side edges 237 of the absorbent assembly 200 in longitudinally extending adhesive attachment zones 29. Alternatively, the upper covering sheet 24 and the lower covering sheet 25 may be attached together in places other than the side edges 237, e.g., at or adjacent to the end edges 236 and 238 of the absorbent assembly 200, or at or adjacent to both the end edges 236 and 238 and the side edges 237. Both the upper covering sheet and the lower covering sheet are water vapor-permeable, i.e., breathable.

The upper covering sheet 24 may be water-permeable and may allow liquid waste to pass through to the absorbent core 250, where the liquid waste may be absorbed. The lower covering sheet 25 may be water-impermeable. However, alternatively, the lower covering sheet 25 may be water-permeable.

In the exemplary absorbent assembly 200 shown in FIGS. 12, 13, 14 and 15, the upper covering sheet 24 and the lower covering sheet 25 are of the same size, i.e., both the upper covering sheet 24 and the lower covering sheet 25 extend to the front edge 236 and back edge 238, as well as to the side edges 237 of the absorbent assembly 200. Alternatively, the upper covering sheet 24 and the lower covering sheet 25 may differ in size.

As another example, the upper covering sheet 24 may be larger than the lower covering sheet 25 and may be wrapped over the side edges 257 of the absorbent core 250 onto the interior surface of the absorbent core 250, where the upper covering sheet 24 and the lower covering sheet 25 may be attached together. Alternatively, in place of a separate upper covering sheet 24 and a separate lower covering sheet 25, a single covering sheet may be wrapped around the absorbent core 250 and attached to itself to contain the absorbent core 250.

The absorbent core 250 includes a storage component 272 that serves to absorb and retain liquid bodily waste materials. Suitable known materials for the absorbent core storage component include cellulose fibers in the form of comminuted wood pulp, commonly known as "airfelt", natural or synthetic fibrous materials, and superabsorbent polymers, used either singly or in mixtures and commonly formed into layers or sheets, etc.

The absorbent core may include an acquisition component in addition to one or more storage components. The absorbent core acquisition component serves to acquire deposited liquid bodily waste material and transfer it to the absorbent core storage component. Any porous absorbent material which will imbibe and partition liquid bodily waste material to the storage component or components may be used to form the acquisition component. Examples of such acquisition materials are more fully described in U.S. Pat. No. 4,950,264 issued to Osborn on Aug. 21, 1990.

Such an absorbent core acquisition component 290 is shown overlying the absorbent core storage component 272 in FIG. 15. A separation sheet 292 of, e.g., a tissue or a nonwoven material, may be disposed between the absorbent core storage component 272 and the absorbent core acquisition component 290 to help ensure that none of the gel formed by a superabsorbent polymer that may be included in the absorbent core storage component reaches the skin of the wearer.

Statements of Incorporation by Reference and Intended Scope of Claims

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
an absorbent assembly comprising an absorbent core;
a chassis formed by a web comprising at least one continuous layer that forms a portion of a water-impermeable backsheet and a portion of laterally opposing, inwardly folded side flaps;
the chassis further comprising a longitudinal axis, a lateral axis, a front waist region comprising a front waist edge, a back waist region comprising a back waist edge, a crotch region between the waist regions, laterally opposing side edges extending between the front waist edge and the back waist edge, an exterior surface, and an interior surface to which the absorbent assembly is attached;
each of the side flaps comprise a longitudinally extending first elastic gathering member attached at or adjacent to its proximal edge to form barrier cuff flaps;
at least one abdominal stretch panel attached to the interior surface or the exterior surface of the chassis in the front waist region or the back waist region and having a circumferentially extending longitudinally distal edge disposed at or adjacent to the respective waist edge and a longitudinally opposing circumferentially extending longitudinally proximal edge, the at least one abdominal stretch panel providing a circumferential contractive force around the waist opening when the chassis is stretched circumferentially; and
the chassis further comprises a continuously activated region disposed in one or both of the front and back waist regions of the article, the continuously activated region comprising longitudinally oriented ridges and valleys, wherein the continuously activated region overlaps the portion of the chassis where the at least one abdominal stretch panel is disposed.

2. The disposable absorbent article of claim 1, wherein the chassis comprises a first activation pattern in the front waist region and/or the back waist region, and wherein the crotch region of the chassis is not activated or comprises a second activation pattern which is different from the first activation pattern.

3. The absorbent article of claim 1, wherein the chassis further comprises an intermittently activated region disposed in the crotch region, the intermittently activated region comprising alternating altered and unaltered regions.

4. The absorbent article of claim 1, wherein a portion of the chassis in one of the front and back waist regions is laterally extensible to a greater extent than a portion of the chassis disposed in the crotch region.

5. The absorbent article of claim 1, wherein a portion of the web in one of the front and back waist regions is deformed to a greater extent than a portion of the chassis disposed in the crotch region.

6. The absorbent article of claim 1, wherein a portion of the web in at least one of the waist regions and in the crotch region comprises ridges and valleys and wherein the ridges and valleys in one or both of the front and back waist regions comprises deeper ridges and valleys than in the crotch region.

7. The absorbent article of claim 1, wherein the continuously activated region disposed in one or both of the front and back waist regions is formed in a shape, the shape comprising a first portion disposed adjacent the side edges of the chassis and having a greater longitudinal length than a second portion disposed in a laterally central portion of the chassis.

8. The absorbent article of claim 1, wherein the interior surface of the chassis comprises longitudinally extending corrugations disposed in the waist region at or adjacent the waist end edge.

9. The absorbent article of claim 1, wherein the absorbent assembly is attached to the interior surface of the chassis via a shaped attachment zone, the shaped attachment zone comprising a convex shape in at least one of the front and back waist regions.

10. The absorbent article of claim 9, wherein the continuously activated region is disposed in one or both of the front and back waist regions comprises a concave shape that is complimentary to the shape of the shaped attachment zone.

11. An absorbent article comprising:
an absorbent assembly comprising an absorbent core;
a chassis comprising a longitudinal axis, a lateral axis, a front waist region comprising a front waist edge, a back waist region comprising a back waist edge, a crotch region between the waist regions, laterally opposing side edges extending between the front waist edge and the back waist edge, the side edges comprising folded side edge segments disposed in the front and back waist regions and cut side edge segments disposed in the crotch region, an exterior surface, and an interior surface to which the absorbent assembly is attached, the chassis comprising a web that forms a portion of a water-impermeable backsheet and a portion of laterally opposing, inwardly folded side flaps, each of the side flaps comprising a longitudinally extending first elastic gathering member attached at or adjacent to its proximal edge to form barrier cuff flaps;
at least one abdominal stretch panel attached to the interior surface or the exterior surface of the chassis in the front waist region or the back waist region and having a circumferentially extending longitudinally distal edge disposed at or adjacent to the respective waist edge and a longitudinally opposing circumferentially extending longitudinally proximal edge, the at least one abdominal stretch panel providing a circumferential contractive force around the waist opening when the chassis is stretched circumferentially; and
the chassis further comprises a continuously activated region disposed in one or both of the front and back waist regions of the article, the continuously activated region comprising longitudinally oriented ridges and valleys, wherein the continuously activated region overlaps the portion of the chassis where the at least one abdominal stretch panel is disposed.

12. The absorbent article of claim 11, wherein the continuously activated region is disposed in one or both of the front and back waist regions is formed in a shape, the shape comprising a first portion disposed adjacent the side edges of the chassis and having a greater longitudinal length than a second portion disposed in a laterally central portion of the chassis.

13. The absorbent article of claim 11, wherein the interior surface of the chassis comprises longitudinally extending corrugations disposed in the waist region at or adjacent the waist region.

14. The absorbent article of claim 11, wherein a portion of the web in one or both of the front and back waist regions exhibits a higher level of deformation than a portion of the chassis disposed in the crotch region.

15. The absorbent article of claim 11, wherein a portion of the chassis in one or both of the front and back waist regions is laterally extensible to a greater extent than a portion of the chassis disposed in the crotch region.

16. The absorbent article of claim 11, wherein a portion of the chassis in one or both of the front and back waist regions comprises ring roll activation and a portion of the chassis disposed in the crotch region comprises no activation.

17. The absorbent article of claim 11, wherein a portion of the web in one or both of the front and back waist regions is ring roll activated and a portion of the web disposed in the crotch region is activated to be a structured elastic-like formed web.

18. The disposable absorbent article of claim 11, wherein the chassis comprises a first activation pattern in the front waist region and/or the back waist region, and wherein the crotch region of the chassis comprises a second activation pattern which is different from the first activation pattern.

19. The disposable absorbent article of claim 11, wherein the absorbent article comprises a closure member, the closure member maintaining the waist and leg openings of the absorbent article in a closed configuration to form a pant.

20. The disposable absorbent article of claim 16, wherein the closure member is refastenable.

* * * * *